US012421316B2

(12) United States Patent
Wang et al.

(10) Patent No.: US 12,421,316 B2
(45) Date of Patent: Sep. 23, 2025

(54) BISPECIFIC IMMUNOTOXINS TARGETING HUMAN CD25+CCR4+ TUMORS AND REGULATORY T-CELLS

(71) Applicant: The Regents of the University of Colorado, Denver, CO (US)

(72) Inventors: Zhirui Wang, Denver, CO (US); Christene Huang, Denver, CO (US); David Mathes, Englewood, CO (US); Elizabeth Pomfret, Cherry Hills Village, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 1012 days.

(21) Appl. No.: 17/431,853

(22) PCT Filed: Feb. 19, 2020

(86) PCT No.: PCT/US2020/018922

§ 371 (c)(1),
(2) Date: Aug. 18, 2021

(87) PCT Pub. No.: WO2020/172344

PCT Pub. Date: Aug. 27, 2020

(65) Prior Publication Data

US 2022/0127368 A1 Apr. 28, 2022

Related U.S. Application Data

(60) Provisional application No. 62/807,676, filed on Feb. 19, 2019.

(51) Int. Cl.

| | |
|---|---|
| ***C07K 16/28*** | (2006.01) |
| ***A61K 45/06*** | (2006.01) |
| ***A61P 35/00*** | (2006.01) |
| ***C07K 14/34*** | (2006.01) |
| ***C07K 14/55*** | (2006.01) |

(52) U.S. Cl.

CPC .......... *C07K 16/2866* (2013.01); *A61K 45/06* (2013.01); *A61P 35/00* (2018.01); *C07K 14/34* (2013.01); *C07K 14/55* (2013.01); *C07K 2319/55* (2013.01)

(58) Field of Classification Search

CPC .... C07K 16/2866; C07K 14/34; C07K 14/55; C07K 2319/55; C07K 2317/622; C07K 2319/00; C07K 2319/33; A61K 45/06; A61P 35/00

See application file for complete search history.

(56) References Cited

U.S. PATENT DOCUMENTS

| | | | | |
|---|---|---|---|---|
| 4,545,985 | A | 10/1985 | Pastan et al. | |
| 4,818,700 | A | 4/1989 | Cregg et al. | |
| 4,892,827 | A | 1/1990 | Pastan et al. | |
| 5,458,878 | A | 10/1995 | Pastan et al. | |
| 5,843,711 | A | 12/1998 | Collier et al. | |
| 7,314,632 | B1 | 1/2008 | Fitzgerald | |
| 7,479,389 | B2 | 1/2009 | Nett et al. | |
| 7,514,253 | B2 | 4/2009 | Nett | |
| 7,585,942 | B2 | 9/2009 | Harrison et al. | |
| 7,696,338 | B2 | 4/2010 | Neville et al. | |
| 7,892,786 | B2 | 2/2011 | Neville et al. | |
| 9,764,006 | B2 | 9/2017 | Wang et al. | |
| 10,675,349 | B2 * | 6/2020 | Marasco | C07K 16/18 |
| 2008/0166375 | A1 | 7/2008 | Leppla et al. | |
| 2009/0010966 | A1 | 1/2009 | Davis et al. | |
| 2009/0012400 | A1 | 1/2009 | Guracar et al. | |
| 2009/0041797 | A1 | 2/2009 | Davis et al. | |
| 2009/0214533 | A1 | 8/2009 | Clynes | |
| 2009/0221500 | A1 | 9/2009 | Davis et al. | |
| 2017/0121419 | A1 | 5/2017 | Wang et al. | |
| 2017/0290911 | A1 | 10/2017 | Marasco et al. | |
| 2018/0118823 | A1 | 5/2018 | Thompson et al. | |

FOREIGN PATENT DOCUMENTS

| | | | |
|---|---|---|---|
| WO | 2009085135 | A3 | 12/2009 |
| WO | 2011046855 | A1 | 4/2011 |
| WO | 2020172344 | A1 | 8/2020 |

OTHER PUBLICATIONS

ISR and Written Opinion mailed Jul. 15, 2020 in International Application No. PCT/US2020/018922, Jul. 15, 2020.

"Database Geneseq "Bivalent anti-human CCR4 immunotoxin D1390-biscFv(1567) construct.", retrieved from EBI accession No. GSP:BCK03558 Database accession No. BCK03558 ; & WO 2015/191997 A 1 (Gen Hospital Corp [US]) 17", Database Geneseq [Online] Feb. 11, 2016 (Feb. 11, 2016), "Bivalent anti-human CCR4 immunotoxin DT390-biscFv(1567) construct.", retrieved from EBI accession No. GSP:BCK03558.

"Database Geneseq Human interleukin 2 (IL-2) fusion toxin (DT390-bi-hIL-2-6xHis), SEQ 31.", retneved from EBT accession No. GSP:BBI67355 Database accession No. BBI67355 ; & WO 2014/093240 A 1 (Gen Hospital Corp [US]), Database Geneseq [Online] Aug. 14, 2014 (Aug. 14, 2014), "Human interleukin 2 (IL-2) fusion toxin (DT390-bi-hIL-2-6xHis), SEQ 31.", retrieved from EBI accession No. GSP:BBI67355.

"European Search Report (EESR) Mailed Nov. 24, 2022 [EP 20758888.0]", Mailed Nov. 24, 2022, 9 pgs.

(Continued)

*Primary Examiner* — Jeffrey Stucker
*Assistant Examiner* — Sarah Cooper Patterson
(74) *Attorney, Agent, or Firm* — Dorsey & Whitney LLP

(57) ABSTRACT

IL2-CCR4 bispecific immunotoxin, CCR4-IL2 bispecific immunotoxin, and methods of use thereof for treatment of refractory and recurrent human $CD25^+$ and/or $CCR4^+$ cutaneous T cell lymphoma, and other human $CD25^+$ or $CCR4^+$ tumors. The bispecific immunotoxin can be also used for broad cancer treatment via depleting $CD25^+$ or $CCR4^+$ Tregs.

20 Claims, 16 Drawing Sheets

Specification includes a Sequence Listing.

(56) References Cited

OTHER PUBLICATIONS

Abi-Habib, Ralph J, et al., "A urokinase-activated recombinant diphtheria toxin targeting the granulocyte-macrophage colony-stimulating factor receptor is selectively cytotoxic to human acute myeloid leukemia blasts", Ralph J. Abi-Habib, A urokinase-activated recombinant diphtheria toxin targeting the granulocyte-macrophage colony-stimulating factor receptor is selectively cytotoxic to human acute myeloid leukemia blasts, Blood, 104(7), 2004, pp. 2143-2148, 2004, pp. 2143-2148.
Aullo P, et al., "A recombinant diphtheria toxin related human CD4 fusion protein specifically kills HIV infected cells which express gp120 but selects fusion toxin resistant cells which carry HIV", Aullo, P. et al. (1992), A recombinant diphtheria toxin related human CD4 fusion protein specifically kills HIV infected cells which express gp120 but selects fusion toxin resistant cells which carry HIV.. The EMBO Journal, 11: 575-583, pp. 575-583, pp. 575-583.
Cereghino, Joan Lin, et al., "Heterologous protein expression in the methylotrophic yeast *Pichia pastoris*", Joan in Cereghino, James M. Cregg, Heterologous protein expression in the methylotrophic yeast *Pichia pastoris*, FEMS Microbiology Reviews, vol. 24, Issue 1, Jan. 2000, pp. 45-66, Jan. 2000, pp. 45-66.
Chang , et al., "Humanization of an anti-CCR4 antibody that kills cutaneous T-cell lymphoma cells and abrogates suppression by T-regulatory cells", Chang DK. Humanization of an anti-CCR4 antibody that kills cutaneous T-cell lymphoma cells and abrogates suppression by T-regulatory cells. Mol Cancer Ther. Nov. 2012;11(11):2451-61., 2012, pp. 2451-2461.
Chaudhary , et al., "Pseudomonas exotoxin contains a specific sequence at the carboxyl terminus that is required for cytotoxicity", Chaudhary et al., "Pseudomonas exotoxin contains a specific sequence at the carboxyl terminus that is required for cytotoxicity" Proc. Nadl. Acad. Sci. USA, vol. 87, pp. 308-312, 1990, 1990, pp. 308-312.
Debinski et al. "Substitution of foreign protein sequences into a chimeric toxin composed of transforming growth factor alpha and Pseudomonas exotoxin." Molecular and cellular biology 11.3 (1991): 1751-1753., 1991, pp. 1751-1753.
Ferenczi Katalin, et al., "Increased CCR4 Expression in Cutaneous T Cell Lymphoma", Katalin Ferenczi, Increased CCR4 Expression in Cutaneous T Cell Lymphoma, Journal of Investigative Dermatology, vol. 119, Issue 6, 2002, pp. 1405-1410,, 2002, pp. 1405-1410.
Foss Francine, "DAB389IL-2 (Denileukin Diftitox, ONTAK): A New Fusion Protein Technology", "DAB389IL-2 (Denileukin Diftitox, ONTAK): A New Fusion Protein Technology", Clincial Lymphoma, Myeloma & Leukemia, vol. 1, No. Suppl. 1, Nov. 1, 2000 (Nov. 1, 2000), pp. S27-S31, Nov. 2000, pp. S27-S31.
Heimbrook, David C, et al., "Transforming growth factor alpha-Pseudomonas exotoxin fusion protein prolongs survival of nude mice bearing tumor xenografts", Heimbrook, David C., et al. "Transforming growth factor alpha-Pseudomonas exotoxin fusion protein prolongs survival of nude mice bearing tumor xenografts." Proceedings of the National Academy of Sciences 87.12 (1990): 4697-4701., 1990, pp. 4697-4701.
Ishida, T , et al., "CCR4 as a novel molecular target for immunotherapy of cancer. Cancer Science, 97: 1139-1146", Ishida, T. and Ueda, R. (2006), CCR4 as a novel molecular target for immunotherapy of cancer. Cancer Science, 97: 1139-1146, 2006, pp. 1139-1146.
Jiang Tao, et al., "Role of IL-2 in cancer immunotherapy", Tao Jiang, Caicun Zhou & Shengxiang Ren (2016) Role of IL-2 in cancer immunotherapy, OncoImmunology, 5:6,, 2016.
Kim, Geun-Bae , et al., "A fold-back single-chain diabody format enhances the bioactivity of an anti-monkey CD3 recombinant diphtheria toxin-based immunotoxin", Geun-Bae Kim, A fold-back single-chain diabody format enhances the bioactivity of an anti-monkey CD3 recombinant diphtheria toxin-based immunotoxin, Protein Engineering, Design and Selection, vol. 20, Issue 9, Sep. 2007, pp. 425-432, 2007, pp. 425-432.
Liu, Yuan Yi, et al., "Targeted introduction of a diphtheria toxin resistant mutation into the chromosomal EF-2 locus of Pichia pastoris and expression of immunotoxin in the EF-2 mutants", Liu et al. Targeted introduction of a diphtheria toxin resistant mutation into the chromosomal EF-2 locus of Pichia pastoris and expression of immunotoxin in the EF-2 mutants, Protein Expression and Purification, vol. 30, Issue 2, 2003, pp. 262-274, 2003, pp. 262-274.
Nichols, J , et al., "Interleukin-2 fusion protein: An investigational therapy for interleukin-2 receptor expressing malignancies", Nichols, J. et al., Interleukin-2 fusion protein: An investigational therapy for interleukin-2 receptor expressing malignancies, Eur J Cancer 33 Suppl 1, S34-6, 1997, 1997, pp. S34-S36.
Ollila , et al., "Mogamulizumab: a new tool for management of cutaneous T-cell lymphoma", Ollila TA, Sahin I, Olszewski AJ. Mogamulizumab: a new tool for management of cutaneous T-cell lymphoma. Onco Targets Ther. Feb. 7, 2019;12:1085-1094., 2019, pp. 1085-1094.
Peraino , et al., "Development of a diphtheria toxin-based recombinant porcine IL-2 fusion toxin for depleting porcine CD25+ cells", Peraino et al., 2013, Development of a diphtheria toxin-based recombinant porcine IL-2 fusion toxin for depleting porcine CD25+ cells. J Immunol Methods. Dec. 15, 2013;398-399:33-43, 2013, pp. 398-399.
Peraino , et al., "Diphtheria toxin-based bivalent human IL-2 fusion toxin with improved efficacy for targeting human CD25(+) cells", Peraino et al., 2014, Diphtheria toxin-based bivalent human IL-2 fusion toxin with improved efficacy for targeting human CD25(+) cells. J Immunol Methods. Mar. 2014;405:57-66., 2014, pp. 57-66.
Peraino , et al., "Expression and characterization of recombinant soluble porcine CD3 ectodomain molecules: mapping the epitope of an anti-porcine CD3 monoclonal antibody", Peraino JS, Expression and characterization of recombinant soluble porcine CD3 ectodomain molecules: mapping the epitope of an anti-porcine CD3 monoclonal antibody 898H2-6-15. Cell Immunol. Mar.-Apr. 2012;276(1-2):162-7, 2012, pp. 162-167.
Perentesis , et al., "Expression of diphtheria toxin fragment A and hormone-toxin fusion proteins in toxin-resistant yeast mutants", Perentesis et al, Expression of diphtheria toxin fragment A and hormone-toxin fusion proteins in toxin-resistant yeast mutants., Proc. Nati. Acad. Sci. USA 85, 8386-8390, 1988, 1988, pp. 8386-8390.
Romanos, Michael A, et al., "Foreign gene expression in yeast: a review", Romanos, Michael A., Carol A. Scorer, and Jeffrey J. Clare. "Foreign gene expression in yeast: a review." Yeast 8.6 (1992): 423-488., 1992, pp. 423-488.
Song, Shuichuan , et al., "Preparation and characterization of fusion protein truncated Pseudomonas Exotoxin A (PE38KDEL) in *Escherichia coli*", Protein Expression and Purification, vol. 44, Issue 1, 2005, pp. 52-57,, 2005, pp. 52-57, 2005, pp. 52-57.
Sugiyama, Daisuke , et al., "Anti-CCR4 mAb selectively depletes effector-type FoxP3+ CD4+ regulatory T cells, evoking antitumor immune responses in humans", Sugiyama, Daisuke, et al. "Anti-CCR4 mAb selectively depletes effector-type FoxP3+ CD4+ regulatory T cells, evoking antitumor immune responses in humans." Proceedings of the National Academy of Sciences 110.44 (2013): 17945-17950., 2013, pp. 17945-17950.
Talpur, Rakhshandra , et al., "CD25 expression is correlated with histological grade and response to denileukin diftitox in cutaneous T-cell lymphoma.", Talpur, Rakhshandra, et al. "CD25 expression is correlated with histological grade and response to denileukin diftitox in cutaneous T-cell lymphoma." Journal of investigative dermatology 126.3 (2006): 575-583., 2006, pp. 575-583.
Theuer, Charles , et al., "A recombinant form of Pseudomonas exotoxin directed at the epidermal growth factor receptor that is cytotoxic without requiring proteolytic processing", Theuer, Charles P. "A recombinant form of Pseudomonas exotoxin directed at the epidermal growth factor receptor that is cytotoxic without requiring proteolytic processing." Journal of Biological Chemistry 267.24 (1992): 16872-16877., 1992, pp. 16872-16877.
Vallera, A , et al., "Genetic alteration of a bispecific ligand directed toxin targeting human CD19 and CD22 receptors resulting in improved efficacy against systemic B cell malignancy", Vallera Da et al: "Genetic alteration of a bispecific ligand-directed toxin

(56) References Cited

OTHER PUBLICATIONS targeting human CD19 and CD22 receptors resulting in improved efficacy against systemic B cell malignancy", Leukemia Research, New York,NY, US,, Sep. 2009, 1233-1242.

Wang , et al., "Bispecific human IL2-CCR4 immunotoxin targets human cutaneous T-cell lymphoma", Wang et al., 2020, Bispecific human IL2-CCR4 immunotoxin targets human cutaneous T-cell lymphoma. Mol Oncol. May 2020;14(5):991-1000, 2020, pp. 991-1000.

Wang Zhirui, et al., "Development of a diphtheria toxin based antiporcine CD3 recombinant immunotoxin", Wang, Zhirui, et al. "Development of a diphtheria toxin based antiporcine CD3 recombinant immunotoxin." Bioconjugate chemistry 22.10 (2011): 2014-2020., 2011, pp. 2014-2020.

Wang , et al., "Diphtheria-toxin based anti-human CCR4 immunotoxin for targeting human CCR4(+) cells in vivo", Wang et al., 2015, Diphtheria-toxin based anti-human CCR4 immunotoxin for targeting human CCR4(+) cells in vivo. Mol Oncol. Aug. 2015;9(7):1458-70, 2015, pp. 1458-1470.

Wang , et al., "Dosing optimization of CCR4 immunotoxin for improved depletion of CCR4+ Treg in nonhuman primates", Wang et al., 2018, Dosing optimization of CCR4 immunotoxin for improved depletion of CCR4+ Treg in nonhuman primates, Molecular Oncology, Vo. 12, No. 8, pp. 1374-1382, 2018, pp. 1374-1382.

Wang , et al., "Ontak-like human IL-2 fusion toxin", Wang et al., 2017, Ontak-like human IL-2 fusion toxin. J Immunol Methods. Sep. 2017;448:51-58, 2017, pp. 51-58.

Wang , et al., "Treg depletion in non-human primates using a novel diphtheria toxin-based anti-human CCR4 immunotoxin", Wang et al., 2015, Treg depletion in non-human primates using a novel diphtheria toxin-based anti-human CCR4 immunotoxin. Mol Oncol. Apr. 2016;10(4):553-65, 2016, pp. 553-565.

Williams, Diane P, et al., "Cellular processing of the interleukin-2 fusion toxin DAB486-IL-2 and efficient delivery of diphtheria fragment A to the cytosol of target cells requires Arg194", Williams, Diane P., et al. "Cellular processing of the interleukin-2 fusion toxin DAB486-IL-2 and efficient delivery of diphtheria fragment A to the cytosol of target cells requires Arg194." Journal of Biological Chemistry 265.33 (1990): 20673-20677, 1990, pp. 20673-20677.

Woo, Jung Hee , et al., "Gene optimization is necessary to express a bivalent anti-human anti-T cell immunotoxin in Pichia pastoris", Woo, Jung Hee, et al. "Gene optimization is necessary to express a bivalent anti-human anti-T cell immunotoxin in Pichia pastoris." Protein expression and purification 25.2 (2002): 270-282., 2002, pp. 270-282.

Wysocki Robert, et al., "The *Saccharomyces cerevisiae* ACR3 Gene Encodes a Putative Membrane Protein Involved in Arsenite Transport", Robert Wysocki, Piotr Bobrowicz, Stanisław Ułaszewski, the *Saccharomyces cerevisiae* ACR3 Gene Encodes a Putative Membrane Protein Involved in Arsenite Transport, Journal of Biological Chemistry, vol. 272, Issue 48, 1997,pp. 30061-30066,, 1997, pp. 30061-30066.

Yoshie, Osamu , et al., "Frequent expression of CCR4 in adult T-cell leukemia and human T-cell leukemia virus type 1-transformed T cells", Yoshie, Osamu, et al. "Frequent expression of CCR4 in adult T-cell leukemia and human T-cell leukemia virus type 1-transformed T cells." Blood, the Journal of the American Society of Hematology 99.5 (2002): 1505-1511., 2002, pp. 1505-1511.

Zhang, Baojun , et al., "Compatibility of porcine and human interleukin 2: implications for xenotransplantation", Zhang, Baojun, et al. "Compatibility of porcine and human interleukin 2: implications for kenotransplantation." Xenotransplantation 13.5 (2006): 423-432., 2006, pp. 423-432.

Zheng, Qian , et al., "Diphtheria toxin-based anti-human CD 19 immunotoxin for targeting human CD 19+ tumors", Zheng, Qian, et al. "Diphtheria toxin-based anti-human CD 19 immunotoxin for targeting human CD 19+ tumors." Molecular oncology 11.5 (2017): 584-594., 2017, pp. 584-594.

* cited by examiner

IL-2 fusion toxin (59 kDa)
N — DT390 — hIL-2 — C
G₄S

Fold-back CCR4 immunotoxin (96 kDa)
N — DT390 — VL | VH | VL | VH — C
       scFv(1567)   scFv(1567)
G₄S  G₄S  (G₄S)₃  G₄S IL2-CCR4 immunotoxin (86 kDa)
N — DT390 — hIL-2 — VL | VH — C
                       scFv(1567)
G₄S    (G₄S)₃   (G₄S)₃

CCR4-IL2 immunotoxin (86 kDa)
N — DT390 — VL | VH — hIL-2 — C
              scFv(1567)
G₄S   (G₄S)₃  (G₄S)₃

C21 IT IL2 IT CCR4 IT CCR4-IL2 IT

G IL2 IT

H CCR4 IT

I IL2-CCR4 IT

J CCR4-IL2 IT

BISPECIFIC IMMUNOTOXINS TARGETING HUMAN CD25+CCR4+ TUMORS AND REGULATORY T-CELLS

CROSS-REFERENCE TO RELATED APPLICATION

This application is a national entry of PCT/US2020/018922, filed Feb. 19, 2020, entitled "BISPECIFIC IMMUNOTOXINS TARGETING HUMAN CD25+CCR4+ TUMORS AND REGULATORY T-CELLS," which claims the benefit of U.S. Provisional patent application No. 62/807,676, entitled "HUMAN IL2-CCR4 BISPECIFIC IMMUNOTOXINS TARGETING HUMAN CD25+CCR4+ TUMORS AND TREGS," filed on Feb. 19, 2019, and each of which is specifically incorporated by referenced for all it discloses and teaches.

REFERENCE TO SEQUENCE LISTING

This application contains a Sequence Listing in computer readable form (as an ASCII compliant text file) entitled "517709-000019-US Sequence Listing", created on Feb. 19, 2019 having a size of 32 kilobytes. The content of the aforementioned file is hereby incorporated by reference in its entirety.

BACKGROUND

Cutaneous T-cell lymphoma (CTCL) is a type of extranodal non-Hodgkin's lymphoma characterized by skin lesions resulting from infiltration of malignant T lymphocytes. The two main forms of CTCL are Mycosis fungoides and Sezary syndrome. Treatment of early-stage CTCL (IA-IIA) primarily involves the use of skin directed therapies including topical corticosteroids, phototherapy, topical chemotherapy, topical bexarotene, and radiotherapy including localized radiation and total skin electron beam therapy. Refractory early-stage and advanced-stage CTCL (IIB-IV) requires systemic treatment using anti-cancer/chemotherapeutic agents such as bexarotene, vorinostat, denileukin diftitox, romidepsin, brentuximab and mogamulizumab. However, the objective response rate of these treatments remains approximately 30%.

SUMMARY

The present invention is based on the development of bispecific immunotoxins that target the surface markers CC chemokine receptor 4 ("CCR4") and/or IL-2 receptor α-chain ("CD25"), which are highly expressed by cutaneous T-cell lymphomas (CTCL). The efficacy of a CCR4 immunotoxin was compared to the efficacy of an IL2 fusion toxin, and the CCR4 immunotoxin was found to be more effective than the IL2 fusion toxin. Two bispecific immunotoxins were then constructed: 1) an IL2-CCR4 bispecific immunotoxin (SEQ ID NO: 4); and 2) a CCR4-IL-2 bispecific immunotoxin (SEQ ID NO: 2). The bispecific immunotoxins were expressed and purified using a diphtheria-toxin resistant yeast *Pichia pastoris* expression system. SDS-PAGE and Western Blot analysis demonstrated that the bispecific ~86 kDa.

The binding affinity of the biotinylated IL2-CCR4 bispecific immunotoxin and the CCR4-IL2 bispecific immunotoxin to human $CD25^+CCR4^+$ Hut102/6TG was analyzed using flow cytometry. The bispecific immunotoxins showed higher in vitro binding affinity and efficacy than the monospecific immunotoxins. In vivo efficacy of the CCR4 immunotoxin, IL2 fusion toxin, and bispecific immunotoxins was assessed using $CD25^+CCR4^+$ CTCL Hut102/6TG-bearing immunodeficient NSG mouse model. The in vivo efficacy data demonstrated that CCR4 immunotoxin is more effective than IL2 fusion toxin and that the bispecific immunotoxins showed more efficacy and greater tumor response in vivo than either monospecific CCR4 immunotoxin or IL2 fusion toxin alone.

In some embodiments, the present invention includes a bispecific immunotoxin composed of a first part comprising a toxin, linked to a second part comprising the cytokine human interleukin-2 (IL-2), and a third part comprising an anti-human CC chemokine Receptor 4 (CCR4) antibody or fragment thereof, the second part being linked to the third part. In some embodiments, the second part is linked to the third part by a linker. In some embodiments, the first part is linked to the second part. In some embodiments, the first part is linked to the second part by a linker. In some embodiments, the first part is linked to the third part. In some embodiments, the first part is linked to the third part by a linker. In some embodiments, the toxin is diptheria toxin.

In some embodiments, the third part comprises at least one human CCR4-binding domain. In some embodiments, at least one human CCR4-binding domain comprises an antigen-binding portion of an anti-human CCR4 antibody. The antigen-binding portion of the anti-human CCR4 antibody may include VH and VL regions from an anti-human CCR4 antibody. In some embodiments the anti-human CCR4 antibody or fragment thereof is humanized. In some embodiments the anti-human CCR4 antibody is referred to as 1567 or mogamulizumab or KW-0761. In some embodiments, the 1567 may be mouse 1567 (SEQ ID NO: 6) or humanized 1567 (SEQ ID NO: 5), as presented in Chang, D K et al., Mol. Cancer Ther. 11, 2451-2461, 2012.

In some embodiments, the present invention includes a codon-optimized nucleic acid molecule optimized for expression in a methylotropic yeast encoding the bispecific immunotoxin.

In another aspect, the present invention includes a nucleic acid encoding the bispecific immunotoxin. In some embodiments, the present invention includes a vector comprising the nucleic acid molecule. In some embodiments, the present invention includes a host cell expressing the nucleic acid molecule. The host cell may be a methylotropic yeast. The host cell may be a cell of the species *Pichia pastoris.*

In some embodiments, the present invention includes a pharmaceutical composition comprising the bispecific immunotoxin and a physiologically acceptable carrier. The method may include administering to the subject a therapeutically effective amount of the bispecific immunotoxin. In some embodiments, the present invention comprises administering an immunotherapy to the subject.

In another aspect, the present invention includes a method of treating a subject who has a cancer. In some embodiments, the cancer is selected from the group of all $CCR4^+$ and/or CD25+ tumors, and other tumors via regulatory T-cell (Tregs) depletion. In some embodiments the method of treating a subject who has a cancer may include administration of the bispecific immunotoxin in combination with another treatment including; surgery, radiation, chemotherapy, molecularly targeted therapy, immunotherapy, cell therapy or other standard of care.

In some embodiments, the cancer comprises cancer cells that express CD25. In some embodiments, the cancer comprises cancer cells that express CCR4. In some embodiments, the present invention comprises a method of depleting CD25-expressing Tregs in a subject. The method may include administering to the subject an effective amount of the bispecific immunotoxin. In some embodiments, the present invention comprises a method of depleting CCR4-expressing regulatory T cells in a subject. The method may include administering to the subject an effective amount of the bispecific immunotoxin.

In a further aspect, the present invention includes a method of producing an IL2-CCR4 bispecific immunotoxin. The method may include expressing a codon-optimized nucleic acid molecule encoding the bispecific immunotoxin of claim 1 in a methylotropic yeast, and substantially purifying the IL2-CCR4 bispecific immunotoxin, thereby producing the IL2-CCR4 bispecific immunotoxin. In some embodiments, the methylotropic yeast is *Pichia pastoris.*

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
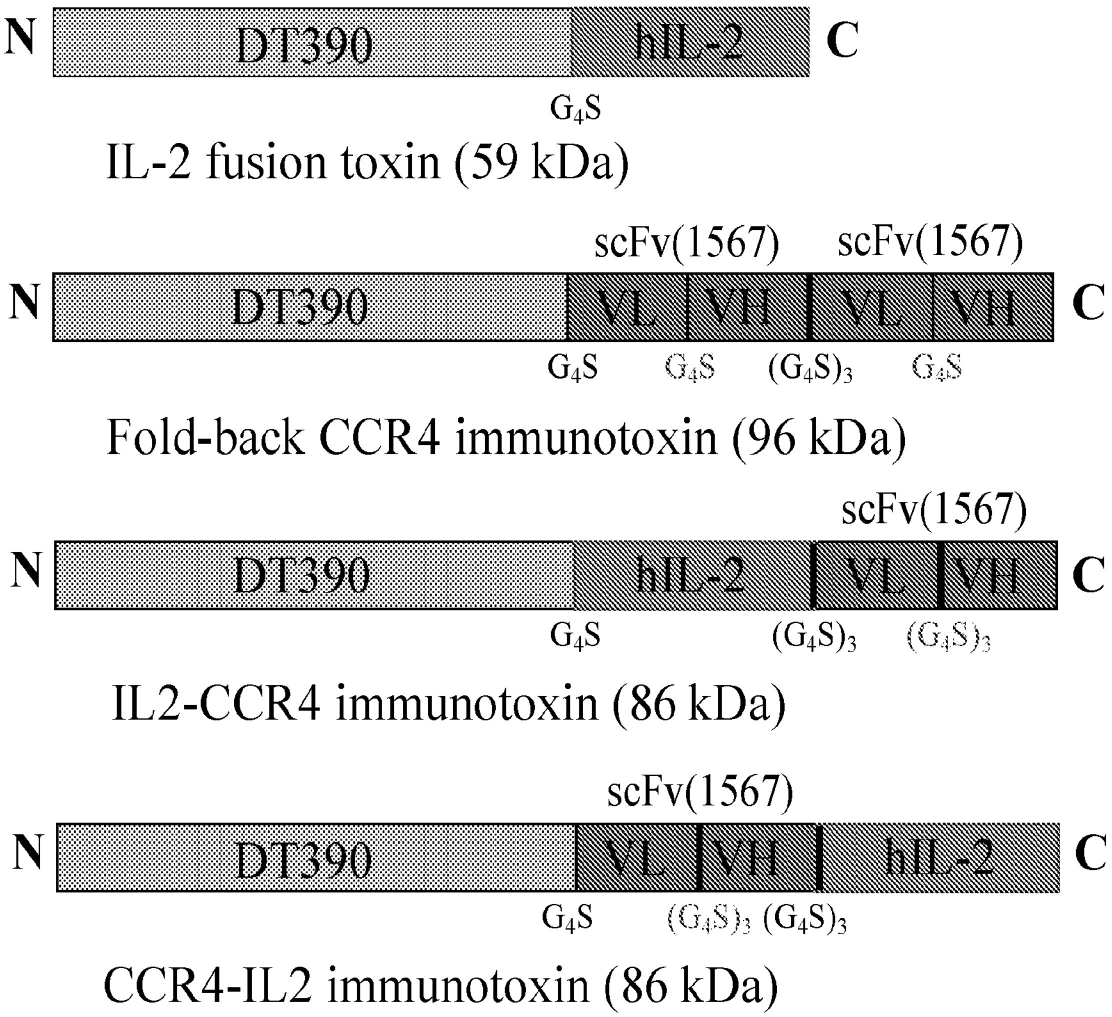
FIG. 1 is a schematic representation of four exemplary toxins in the disclosed technology: 1) a human IL2 fusion toxin; 2) a single-chain foldback diabody anti-human CCR4 immunotoxin; 3) an IL2-CCR4 bispecific immunotoxin; 4) a CCR4-IL2 bispecific immunotoxin.

The majority of clinically diagnosed cutaneous T-cell lymphomas (CTCL) highly express the cell surface markers CC chemokine receptor 4 ("CCR4") and/or IL-2 receptor α-chain ("CD25"). CCR4 is overexpressed in CTCL skin lesions at all stages of disease and is recognized as a therapeutic target for CTCL (Sugaya, M., et al., *J. Dermatol.* 42, 1-3, 2015; Ferenczi, K. et al., *J. Invest. Dermatol.* 119, 1405-1410, 2002). Immunohistochemical CCR4 expression is 14-97% in the skin of CTCL patients and 90-100% in the clinical trials enrolling patients with relapsed diseases. CCR4 is detectable in almost all of the CTCL cases involving the blood using flow cytometry and percentages of CCR4 positive cells range from 31% to 97%. This is significantly higher than among healthy individuals (27%) (Ollila, T A, et al., *Onco Targets Ther.* 12, 1085-1094, 2019).

Although CD25 is expressed in fewer CTCL cases than CCR4, it is recognized as an important therapeutic target. Nichols, J. et al., *Eur J Cancer* 33 *Suppl* 1, S34-6, 1997 reported that CD25 is expressed in ~50% of CTCL cases. CD25 expression is found more commonly in lesions from advanced CTCL patients (Talpur, R. et al., *J. Invest Dermatol.* 126, 575-83, 2006).

Previously, a recombinant anti-human CCR4 immunotoxin for targeting $CCR4^+$ tumors and Tregs was developed using a unique diphtheria toxin resistant yeast *Pichia pastoris* expression system (Wang, Z. et al., *Mol. Oncol.* 9, 1458-1470, 2015). The efficacy for targeting $CCR4^+$ tumors was characterized using a $CCR4^+$ T-cell acute lymphoblastic leukemia tumor-bearing immunodeficient NSG mouse model (Wang et al., 2015). The $CCR4^+$ Treg depletion efficacy was demonstrated using naïve cynomolgus monkeys (Wang, Z. et al., *Mol. Oncol.* 10, 553-565, 2016; Wang, Z. et al., *Mol. Oncol.* 12, 1374-1382, 2018). A human IL-2 fusion toxin (IL2 fusion toxin) was developed using a diphtheria toxin resistant yeast *Pichia pastoris* expression system (Liu, Y Y et al., *Protein Expr. Purif.* 30, 262-274, 2003) and characterized its efficacy in vitro and in vivo (Peraino, J S et al., *J. Immunol. Methods* 405, 57-66, 2014; Wang, et al., *J. Immunol. Methods* 448, 51-58, 2017).

In the present invention, the efficacy of the human IL2 fusion toxin and the anti-human CCR4 immunotoxin described above were compared for targeting human $CD25^+$ $CCR4^+$ CTCL. The CCR4 immunotoxin was more effective than the IL2 fusion toxin. Then, an IL2-CCR4 bispecific immunotoxin (SEQ ID NO: 4) and a CCR4-IL2 bispecific immunotoxin (SEQ ID NO: 2) were constructed. The bispecific immunotoxins were significantly more effective than either IL2 fusion toxin or CCR4 immunotoxin alone. The bispecific immunotoxins are targeted therapeutic drug candidates for the treatment of refractory and recurrent human $CD25^+$ and/or $CCR4^+$ CTCL.

The exemplary reagents constructed under this disclosure are generated by; 1) linking one, two or more, IL-2 polypeptides to a toxin, e.g., the truncated diphtheria toxin (DT390) for the human IL2 fusion toxin; 2) linking one or two anti-human CCR4 scFv polypeptides to a toxin, e.g., the truncated diphtheria toxin (DT390) for the CCR4 immunotoxin; and 3) linking IL-2 polypeptides, a toxin, and anti-human CCR4 scFv polypeptides, in varying order, for a bispecific immunotoxin.

In one embodiment (SEQ ID NO: 1), DT390 (SEQ ID NO: 7) was linked to anti-human CCR4 scFv, and the anti-human CCR4 scFv was linked to human IL2, as described below. DT390 (SEQ ID NO: 7) was linked to anti-human CCR4 scFv VL (SEQ ID NO: 9) via a linker sequence (SEQ ID NO: 8). Anti-human CCR4 scFv VL (SEQ ID NO: 9) was linked to anti-human CCR4 scFv VH (SEQ ID NO: 11) by a linker (SEQ ID NO: 10); and human IL2 (SEQ ID NO: 13) was linked to the anti-human CCR4 scFv VH (SEQ ID NO:11) by a linker (SEQ ID NO: 12).

```
SEQ ID NO: 7:
GCT GGT GCT GAC

GACGTCGTCGACTCCTCCAAGTCCTTCGTCATGGAGAACTTCGCTTCCTACCACG

GGACCAAGCCAGGTTACGTCGACTCCATCCAGAAGGGTATCCAGAAGCCAAAGT

CCGGCACCCAAGGTAACTACGACGACGACTGGAAGGGGTTCTACTCCACCGACA

ACAAGTACGACGCTGCGGGATACTCTGTAGATAATGAAAACCCGCTCTCTGGAA
```

-continued

AAGCTGGAGGCGTGGTCAAGGTCACCTACCCAGGTCTGACTAAGGTCTTGGCTTT

GAAGGTCGACAACGCTGAGACCATCAAGAAGGAGTTGGGTTTGTCCTTGACTGA

GCCATTGATGGAGCAAGTCGGTACCGAAGAGTTCATCAAGAGATTCGGTGACGG

TGCTTCCAGAGTCGTCTTGTCCTTGCCATTCGCTGAGGGTTCTTCTAGCGTTGAAT

ATATTAATAACTGGGAACAGGCTAAGGCTTTGTCTGTTGAATTGGAGATTAACTT

CGAAACCAGAGGTAAGAGAGGTCAAGATGCGATGTATGAGTATATGGCTCAAGC

CTGTGCTGGTAACAGAGTCAGACGTTCTGTTGGTTCCTCTTTGTCCTGTATCAACC

TAGACTGGGACGTCATCAGAGACAAGACTAAGACCAAGATCGAGTCTTTGAAAG

AGCATGGCCCAATCAAGAACAAGATGTCCGAATCCCCCGCTAAGACCGTCTCCG

AGGAAAAGGCCAAGCAATACCTAGAAGAGTTCCACCAAACCGCCTTGGAGCATC

CTGAATTGTCAGAACTTAAAACCGTTACTGGGACCAATCCTGTATTCGCTGGGGC

TAACTATGCGGCGTGGGCAGTAAACGTTGCGCAAGTTATCGATAGCGAAACAGC

TGATAATTTGGAAAAGACAACTGCTGCTCTTTCGATACTTCCTGGTATCGGTAGC

GTAATGGGCATTGCAGACGGTGCCGTTCACCACAATACAGAAGAGATAGTGGCA

CAATCCATCGCTTTGTCCTCTTTGATGGTTGCTCAAGCTATCCCATTGGTCGGTGA

GTTGGTTGACATCGGTTTCGCTGCCTACAACTTCGTCGAGTCCATCATCAACTTGT

TCCAAGTCGTCCACAACTCCTACAACCGTCCGGCTTACTCCCCAGGTCACAAGAC

CCAACCATTCTTG CCA TGG

SEQ ID NO: 8:
GGT GGT GGT GGT TCT

SEQ ID NO: 9:
GAC ATT GAG TTG ACT CAA TCT CCA TCT TCC TTG GCT GTT TCT

GCT GGT GAG AAG GTT ACT ATG TCT TGT AAG TCT TCC CAA TCT ATT TTG

TAC TCT TCC AAC CAA AAG AAC TAC TTG GCT TGG TAC CAA CAA AAG CCA

GGT CAA TCT CCA AAG TTG TTG ATT TAC TGG GCT TCT ACT AGA GAG TCT

GGT GTT CCA GAC AGA TTC ACT GGT TCT GGT TCT GGT ACT GAC TTC ACT

TTG ACT ATT TCT TCC GTT CAA GCT GAG GAC TTG GCT GTT TAC TAC TGT

CAC CAA TAC TTG TCT TCC TAC ACT TTC GGT GGT GGT ACT AAG TTG GAG

ATT AAG

SEQ ID NO: 10:
GGT GGT GGT GGT TCT GGT GGT GGT GGA TCT GGT GGT GGT

GGT TCT

SEQ ID NO: 11:
CAA GTT CAA TTG CAA CAA TCT GGT CCA GAG TTG GTT AGA

CCA GGT GCT TCT GTT AGA ATT TCT TGT AAG GCT TCT GGT TAC ACT TTC

GCT TCT TAC TAC ATT CAA TGG ATG AAG CAA AGA CCA GGT CAA GGT TTG

GAG TGG ATT GGT TGG ATT AAC CCA GGT AAC GTT AAC ACT AAG TAC AAC

GAG AAG TTC AAG GGT AAG GCT ACT TTG ACT GCT GAC AAG TCT TCC ACT

ACC GCT TAC ATG CAA TTG TCT TCC TTG ACT TCT GAG GAC TCT GCT GTT

TAC TTC TGT GCT AGA TCc ACT TAC TAC AGA CCA TTG GAC TAC TGG GGT

CAA GGT ACT ACC GTT ACT GTT TCT TCC

-continued

```
SEQ ID NO: 12:
GGT GGT GGT GGT TCT GGT GGT GGT GGA TCC GGT GGT GGT

GGT TCT

SEQ ID NO: 13:
GCT CCA ACT TCT TCT TCT ACT AAG AAG ACT CAA TTG CAA

TTG GAG CAC TTG TTG TTG GAC TTG CAA ATG ATT TTG AAC GGT ATT AAC

AAC TAC AAG AAC CCA AAG TTG ACT AGA ATG TTG ACT TTC AAG TTC TAC

ATG CCA AAG AAG GCT ACT GAG TTG AAG CAC TTG CAA TGT TTG GAG GAG

GAA TTG AAG CCA TTG GAG GAA GTT TTG AAC TTG GCT CAA TCT AAG AAC

TTC CAC TTG AGA CCA AGA GAC TTG ATT TCT AAC ATT AAC GTT ATT GTT

TTG GAG TTG AAG GGT TCT GAG ACT ACT TTC ATG TGT GAG TAC GCT GAC

GAG ACT GCT ACT ATT GTT GAG TTC TTG AAC AGA TGG ATT ACT TTC TGT

CAA TCT ATT ATC TCT ACT TTG ACT CAC CAC CAC CAC CAC CAC
```

This sequence (SEQ ID NO: 1) encoded a human CCR4-IL2 bispecific immunotoxin (SEQ ID NO: 2):

```
(SEQ ID NO: 2):
AGADDVVDSSKSFVMENFASYHGTKPGYVDSIQKGIQKPKSGTQGNYDD

DWKGFYSTDNKYDAAGYSVDNENPLSGKAGGVVKVTYPGLTKVLALKVD

NAETIKKELGLSLTEPLMEQVGTEEFIKRFGDGASRVVLSLPFAEGSSS

VEYINNWEQAKALSVELEINFETRGKRGQDAMYEYMAQACAGNRVRRSV

GSSLSCINLDWDVIRDKTKTKIESLKEHGPIKNKMSESPAKTVSEEKAK

QYLEEFHQTALEHPELSELKTVTGTNPVFAGANYAAWAVNVAQVIDSET

ADNLEKTTAALSILPGIGSVMGIADGAVHHNTEEIVAQSIALSSLMVAQ

AIPLVGELVDIGFAAYNFVESIINLFQVVHNSYNRPAYSPGHKTQPFLP

WGGGGSDIELTQSPSSLAVSAGEKVTMSCKSSQSILYSSNQKNYLAWYQ
```

-continued

```
QKPGQSPKLLIYWASTRESGVPDRFTGSGSGTDFTLTISSVQAEDLAVY

YCHQYLSSYTFGGGTKLEIKGGGGSGGGGSGGGGSQVQLQQSGPELVRP

GASVRISCKASGYTFASYYIQWMKQRPGQGLEWIGWINPGNVNTKYNEK

FKGKATLTADKSSTTAYMQLSSLTSEDSAVYFCARSTYYRPLDYWGQGT

TVTVSSGGGGSGGGGSGGGGSAPTSSSTKKTQLQLEHLLLDLQMILNGI

NNYKNPKLTRMLTFKFYMPKKATELKHLQCLEEELKPLEEVLNLAQSKN

FHLRPRDLISNINVIVLELKGSETTFMCEYADETATIVEFLNRWITFCQ

SIISTLTHHHHHH
```

In another embodiment (SEQ ID NO: 3), DT390 (SEQ ID NO: 14) was linked to human IL2 (SEQ ID NO: 16); human IL2 (SEQ ID NO: 16) was linked to anti-human CCR4 scFv (SEQ ID NO: 18) by a linker (SEQ ID NO: 17), and the anti-human CCR4 scFv VL (SEQ ID NO: 18) was linked to anti-human CCR4 scFv VH (SEQ ID NO: 20) by a linker (SEQ ID NO: 19):

```
SEQ ID NO: 14:
GCT GGT GCT GAC

GACGTCGTCGACTCCTCCAAGTCCTTCGTCATGGAGAACTTCGCTTCCTACCACG

GGACCAAGCCAGGTTACGTCGACTCCATCCAGAAGGGTATCCAGAAGCCAAAGT

CCGGCACCCAAGGTAACTACGACGACGACTGGAAGGGGTTCTACTCCACCGACA

ACAAGTACGACGCTGCGGGATACTCTGTAGATAATGAAAACCCGCTCTCTGGAA

AAGCTGGAGGCGTGGTCAAGGTCACCTACCCAGGTCTGACTAAGGTCTTGGCTTT

GAAGGTCGACAACGCTGAGACCATCAAGAAGGAGTTGGGTTTGTCCTTGACTGA

GCCATTGATGGAGCAAGTCGGTACCGAAGAGTTCATCAAGAGATTCGGTGACGG

TGCTTCCAGAGTCGTCTTGTCCTTGCCATTCGCTGAGGGTTCTTCTAGCGTTGAAT

ATATTAATAACTGGGAACAGGCTAAGGCTTTGTCTGTTGAATTGGAGATTAACTT

CGAAACCAGAGGTAAGAGAGGTCAAGATGCGATGTATGAGTATATGGCTCAAGC

CTGTGCTGGTAACAGAGTCAGACGTTCTGTTGGTTCCTCTTTGTCCTGTATCAACC

TAGACTGGGACGTCATCAGAGACAAGACTAAGACCAAGATCGAGTCTTTGAAAG
```

-continued

AGCATGGCCCAATCAAGAACAAGATGTCCGAATCCCCCGCTAAGACCGTCTCCG

AGGAAAAGGCCAAGCAATACCTAGAAGAGTTCCACCAAACCGCCTTGGAGCATC

CTGAATTGTCAGAACTTAAAACCGTTACTGGGACCAATCCTGTATTCGCTGGGGC

TAACTATGCGGCGTGGGCAGTAAACGTTGCGCAAGTTATCGATAGCGAAACAGC

TGATAATTTGGAAAAGACAACTGCTGCTCTTTCGATACTTCCTGGTATCGGTAGC

GTAATGGGCATTGCAGACGGTGCCGTTCACCACAATACAGAAGAGATAGTGGCA

CAATCCATCGCTTTGTCCTCTTTGATGGTTGCTCAAGCTATCCCATTGGTCGGTGA

GTTGGTTGACATCGGTTTCGCTGCCTACAACTTCGTCGAGTCCATCATCAACTTGT

TCCAAGTCGTCCACAACTCCTACAACCGTCCGGCTTACTCCCCAGGTCACAAGAC

CCAACCATTCTTGCCA TGG

SEQ ID NO: 15:
GGT GGT GGT GGT TCT

SEQ ID NO: 16:
GCT CCA ACT TCT TCT TCT ACT AAG AAG ACT CAA TTG CAA

TTG GAG CAC TTG TTG TTG GAC TTG CAA ATG ATT TTG AAC GGT ATT AAC

AAC TAC AAG AAC CCA AAG TTG ACT AGA ATG TTG ACT TTC AAG TTC TAC

ATG CCA AAG AAG GCT ACT GAG TTG AAG CAC TTG CAA TGT TTG GAG GAG

GAA TTG AAG CCA TTG GAG GAA GTT TTG AAC TTG GCT CAA TCT AAG AAC

TTC CAC TTG AGA CCA AGA GAC TTG ATT TCT AAC ATT AAC GTT ATT GTT

TTG GAG TTG AAG GGT TCT GAG ACT ACT TTC ATG TGT GAG TAC GCT GAC

GAG ACT GCT ACT ATT GTT GAG TTC TTG AAC AGA TGG ATT ACT TTC TGT

CAA TCT ATT ATC TCT ACT TTG ACT

SEQ ID NO: 17:
GGT GGT GGT GGT TCT GGT GGT GGT GGA TCC GGT GGT GGT

GGT TCT

SEQ ID NO: 18:
GAC ATT GAG TTG ACT CAA TCT CCA TCT TCC TTG GCT GTT

TCT GCT GGT GAG AAG GTT ACT ATG TCT TGT AAG TCT TCC CAA TCT ATT

TTG TAC TCT TCC AAC CAA AAG AAC TAC TTG GCT TGG TAC CAA CAA AAG

CCA GGT CAA TCT CCA AAG TTG TTG ATT TAC TGG GCT TCT ACT AGA GAG

TCT GGT GTT CCA GAC AGA TTC ACT GGT TCT GGT TCT GGT ACT GAC TTC

ACT TTG ACT ATT TCT TCC GTT CAA GCT GAG GAC TTG GCT GTT TAC TAC

TGT CAC CAA TAC TTG TCT TCC TAC ACT TTC GGT GGT GGT ACT AAG TTG

GAG ATT AAG

SEQ ID NO: 19:
GGT GGT GGT GGT TCT GGT GGT GGT GGA TCT GGT GGT GGT

GGT TCT

SEQ ID NO: 20:
CAA GTT CAA TTG CAA CAA TCT GGT CCA GAG TTG GTT AGA

CCA GGT GCT TCT GTT AGA ATT TCT TGT AAG GCT TCT GGT TAC ACT TTC

GCT TCT TAC TAC ATT CAA TGG ATG AAG CAA AGA CCA GGT CAA GGT TTG

GAG TGG ATT GGT TGG ATT AAC CCA GGT AAC GTT AAC ACT AAG TAC AAC

GAG AAG TTC AAG GGT AAG GCT ACT TTG ACT GCT GAC AAG TCT TCC ACT

ACC GCT TAC ATG CAA TTG TCT TCC TTG ACT TCT GAG GAC TCT GCT GTT

-continued

```
TAC TTC TGT GCT AGA TCc ACT TAC TAC AGA CCA TTG GAC TAC TGG GGT

CAA GGT ACT ACC GTT ACT GTT TCT TCC CAC CAC CAC CAC CAC CAC
```

This sequence (SEQ ID NO: 3) encoded a human IL2-CCR4 bispecific immunotoxin (SEQ ID NO: 4):

```
SEQ ID NO: 4:
AGADDVVDSSKSFVMENFASYHGTKPGYVDSIQKGIQKPKSGTQGNYDD

DWKGFYSTDNKYDAAGYSVDNENPLSGKAGGVVKVTYPGLTKVLALKVD

NAETIKKELGLSLTEPLMEQVGTEEFIKRFGDGASRVVLSLPFAEGSSS

VEYINNWEQAKALSVELEINFETRGKRGQDAMYEYMAQACAGNRVRRSV

GSSLSCINLDWDVIRDKTKTKIESLKEHGPIKNKMSESPAKTVSEEKAK

QYLEEFHQTALEHPELSELKTVTGTNPVFAGANYAAWAVNVAQVIDSET

ADNLEKTTAALSILPGIGSVMGIADGAVHHNTEEIVAQSIALSSLMVAQ

AIPLVGELVDIGFAAYNFVESIINLFQVVHNSYNRPAYSPGHKTQPFLP

WGGGGSAPTSSSTKKTQLQLEHLLLDLQMILNGINNYKNPKLTRMLTFK

FYMPKKATELKHLQCLEEELKPLEEVLNLAQSKNFHLRPRDLISNINVI

VLELKGSETTFMCEYADETATIVEFLNRWITFCQSIISTLTGGGGSGGG

GSGGGGSDIELTQSPSSLAVSAGEKVTMSCKSSQSILYSSNQKNYLAWY

QQKPGQSPKLLIYWASTRESGVPDRFTGSGSGTDFTLTISSVQAEDLAV

YYCHQYLSSYTFGGGTKLEIKGGGGSGGGGSGGGGSQVQLQQSGPELVR

PGASVRISCKASGYTFASYYIQWMKQRPGQGLEWIGWINPGNVNTKYNE

KFKGKATLTADKSSTTAYMQLSSLTSEDSAVYFCARSTYYRPLDYWGQG

TTVTVSSHHHHHH
```

Without being limited to any one theory, these reagents are believed to function by binding to a cell surface via the IL-2/CD25 interaction and/or the anti-human CCR4 scFv/CCR4 receptor interaction; and the toxin, e.g., DT390 domain, is internalized by the cell. Following internalization, protein synthesis is inhibited, resulting in cell death.

The bispecific immunotoxins showed significantly higher efficacy for human CD25+ CCR4+ cells when compared to the monospecific immunotoxins alone. Without being limited to any one theory, linking human IL-2 fusion toxin and anti-human CCR4 scFv domains in tandem may increase the immunotoxins' affinity for IL-2 and human CCR4, facilitating a more efficient internalization, and causing an increase in potency. Endotoxin is a common concern when using an *E. coli* expression system for production. The present study utilized a diphtheria toxin-resistant yeast *Pichia pastoris* expression system (Liu, Y Y et al., 2003), which offers enhanced protein expression levels, purification and yield. Producing the bispecific immunotoxins in yeast rather than *E. coli* may augment the potential for clinical application of this reagent.

The truncated diphtheria toxin DT390 has been used to build recombinant immunotoxins (Woo et al., *Protein Expr. Purif.* 25, 270-282, 2002; Kim et al., *Protein Eng. Des. Sel.* 20, 425-432, 2007; Wang et al., *Bioconjug Chem.* 22, 2014-2020, 2011). DT390 lacks the cell-surface binding domain and consists of the catalytic and translocation domains of the diphtheria toxin. In some embodiments, the toxin is diphtheria toxin (DT) or portions or variants thereof, e.g., Metl-Thr387, e.g., as described in Aullo et al, *EMBO J.* 11(2), 575-83, 1992; Abi-Habib et al, *Blood* 104(7), 2143-2148, 2004; Perentesis et al, *Proc. Natl. Acad. Sci. USA* 85, 8386-8390, 1988; Zettlemeissl et al, *Gene.* 41(1), 103-111, 1986; US 2009/0010966; US20090041797; U.S. Pat. Nos. 5,843,711; 7,585,942; 7,696,338; or US20080166375. In some embodiments, the toxin may be *Pseudomonas* exotoxin (PE), or portions or variants thereof, e.g., as described in U.S. Pat. Nos. 4,545,985; 4,892,827; 5,458,878; 7,314,632; Song et al, *Protein Expression and Purification* 44(l), 52-57, 2005; Theuer et al, *J. Biol. Chem.* 267(24), 16872-16877, 1992; Heimbrook et al, *Proc Natl Acad Sci USA.* 87(12), 4697-4701, 1990; Debinski et al, *Mol Cell Biol.* 11(3), 1751-1753, 1991; and Chaudhary et al, *Proc. Nadl. Acad. Sci. USA* 87, 308-312, 1990.

IL-2 binds to its cell surface receptor with notably strong affinity. The IL-2 receptor is a trimer composed of three subunits, α-β-γ. The a-subunit of this receptor, also known as CD25, is constitutively expressed on Tregs and has very high affinity for IL-2. There are species differences, which affect CD25 binding and subsequent target cell proliferation and differentiation (Zhang et al., Xenotransplantation 13, 423-32, 2006), thus it is important to match the IL-2 sequence used to the species of the subject to be treated (i.e., use the human IL-2, or a variant thereof (e.g., IL2 mutant) that binds the human IL-2 receptor, to treat human subjects).

Chemokine (C—C motif) receptor 4 (CCR4) is a G protein coupled receptor. It is a receptor for the chemokines, CCL17, and CCL22. CCR4 is constitutively expressed on Tregs and has a very low expression in most other cells of the immune system (Sugiyama et al., *Proc Natl Acad Sci USA* 110, 17945, 2013). Some human cancers (e.g., adult T-cell leukemia/lymphoma (Ishida et al., *Cancer Sci.* 97(11), 1139-1146, 2006); skin homing cutaneous T cell lymphoma (Ferenczi et al., *J. Invest Dermatol* 119(6), 1405-1410, 2002); acute T-cell lymphoblastic leukemia (Yoshie O. et al., *Blood* 99(5), 2002); Cutaneous T cell lymphoma/leukemia (CTCL), anaplastic large cell lymphoma (ALCL), peripheral T cell lymphoma (PTCL); and adult T-cell leukemia/lymphoma (ATLL) Yoshie, O et al., *Int Immunol, epub,* 2014) have also demonstrated high levels of CCR4 expression and can also be treated using methods described herein.

DNA and amino acid sequences are provided herein that include the linkers between DR390 and human IL2/anti-human CCR4 scFv, the linkers between human IL2 and anti-human CCR4 scFv, and the linkers between VL and VH.

The exemplary $(G45)_3$ linker used herein has been successfully used in following immunotoxins: anti-porcine CD3 immunotoxins (Wang et al., 2011); anti-human CD3 immunotoxin (Woo et al. 2002); anti-monkey CD3 immunotoxin (Kim et al, 2007).

Single chain variable fragments are fusion proteins of the variable regions of the heavy (VH) and light (VL) chains of immunoglobulins, connected into a single polypeptide chain with a short linker peptide (e.g., 1-50 or 10-25 amino acids). The linker allows the scFv to fold into a structure suitable for antigen binding. A monovalent construct includes a single ScFv. Two ScFvs can be linked, e.g., using a linker of 1-50, e.g., 10-25, amino acids, to form a divalent construct. Such divalent ScFv fusions include two VH and two VL domains with flexible linkers in between (e.g., VH-linker1-VL-linker2-VH-linker3-VL). In some embodiments, linkers 1 and 3 are the same, and are 10-25 amino acids long, and linker 2 is 15-20.

In some embodiments, the immunotoxins further include a peptide tag useful for purification. In some embodiments, the tag comprises histidines, e.g., two or more, e.g., three, four, five or six histidine residues at the C-terminus, and purification is achieved by binding to a nickel or cobalt column. In some embodiments, the tag comprises glutathione-S-transferase (GST) and recovery is by affinity to substrate glutathione bound to a column, e.g., glutathione sepharose.

The methods for producing immunotoxins described herein can be performed using protein production methods known in the art. For example, for scaled-up production, fermentation expression can be used.

In some embodiments, the methods use *P. pastoris* as a host organism, e.g., wild-type, X33, GS115 (his4), KM71, MC1OO-3, SMD1163, SMD1165, or SMD1168 strain. In other embodiments, other host organisms are contemplated.

Vectors suitable for use in the present methods are known in the art, and generally include a promoter, e.g., an AOX1, a constitutive *P. Pastoris* promoter derived from the *P. Pastoris* glyceraldehyde-3-phosphate dehydrogenase gene (GAP) promoter, typically followed immediately with a DNA sequence that encodes a secretion signal, e.g., the *S. cerevisiae* a factor prepro signal sequence, or the signal sequence derived from the *P. Pastoris* acid phosphatase gene (PHO1).

The vectors can also include one or more yeast selectable markers that can be used to identify and/or select those cells that contain the vector can be used. Such markers can include drug resistance markers and pathways for synthesis of essential cellular components, e.g., nutrients. Drug resistance markers that can be used in yeast include chloramphenicol, kanamycin, methotrexate, G418 (geneticin), Zeocin, and the like. Markers in synthesis pathways can be used with available yeast strains having auxotrophic mutations in the corresponding gene; examples include the pathways for synthesizing leucine (LEU2), tryptophan (TRP1 and TRP2), proline (PRO1), uracil (URA3, URA5, URA6), histidine (HIS3), lysine (LYS2), adenine (ADEJ or ADE2), and the like. Other yeast selectable markers include the ARR3 gene from *S. cerevisiae*, which confers arsenite resistance to yeast cells that are grown in the presence of arsenate (Bobrowicz et al., *Yeast* 13, 819-828, 1997; Wysocki et al, *J. Biol. Chem.* 272, 30061-30066, 1997). A number of suitable integration sites include those enumerated in U.S. Pat. No. 7,479,389 and include homologs to loci known for *Saccharomyces cerevisiae* and other yeast or fungi. Methods for integrating vectors into yeast are well known (See for example, U.S. Pat. Nos. 7,479,389, 7,514,253, U.S. Published Application No. 2009012400, and WO2009/085135). Examples of insertion sites include, but are not limited to, *Pichia* ADE genes; *Pichia* TRP (including TRP J through TRP2) genes; *Pichia* MCA genes; *Pichia* CYM genes; *Pichia* PEP genes; *Pichia* PRB genes; and *Pichia* LEU genes. The *Pichia* ADE 1 and ARG4 genes have been described in Lin Cereghino et al, *Gene* 263, 159-169, 2001, and U.S. Pat. No. 4,818,700, the HIS3 and TRP1 genes have been described in Cosano et al, *Yeast* 14, 861-867, 1998, HIS4 has been described in GenBank Accession No. X5 180. See e.g., WO2011046855; Cregg, J M, *Pichia Protocols* 2(389), 2007; Romanos et al., *Yeast* 8, 423-488, 1992; Ilgen, et al., *Gellissen, G.* (ed.) (7), 143-16, 2004; Cereghino et al., *FEMS Microbiology Reviews* 24, 45-66 (2000); and Cregg, *Research Corporation Technologies.* Exemplary vectors include pPIC3K, pPIC9K, pA0815 and the pPICZ vector series.

Methods known in the art can be used for purification of the bispecific immunotoxins. For example, in one embodiment, a method may include a hexahistidine tag to facilitate purification, followed by ion exchange chromatography. In other embodiments, other methods, including ammonium sulfate precipitation, reversed phase chromatography, hydrophobic interaction chromatography (HIC), size exclusion chromatography, affinity chromatography, metal binding, immunoaffinity chromatography, HPLC, or purification tags (e.g., as described above) may be used to directly capture the purified proteins. See, e.g., Deutscher, M P, *Methods in Enzymology,* 1990; and The Recombinant Protein Handbook, Protein Amplification and Simple Purification, *Amersham Pharmacia Biotech.* After purification, the protein can optionally be concentrated, e.g., by lyophilization or ultrafiltration.

The bispecific immunotoxins described herein can be used in the treatment or study of certain disorders, e.g., blood cancers including; adult T-cell leukemia/lymphoma, skin homing cutaneous T cell lymphoma, acute T-cell lymphoblastic leukemia, cutaneous T cell lymphoma/leukemia, anaplastic large cell lymphoma, peripheral T cell lymphoma, and adult T-cell leukemia/lymphoma and cancers responsive to Treg depletion via CD25+ CCR4+ binding or characterized by CD25+ CCR4+ expression on the tumor cell surface. In some embodiments of this disclosure, the methods are used to treat subjects who have cutaneous T cell lymphoma.

In another embodiment, the bispecific immunotoxins described herein can also be used to target and deplete CD25+CCR4+ Treg cells. Treg cells suppress immune responses to tumors, therefore, methods that target and deplete this cell population in vivo could prove to be useful in improving cancer immunotherapy.

Generally, the methods include administering a therapeutically effective amount of bispecific immunotoxins as described herein, alone or in combination with another active or therapeutic agent, to a subject who is in need of, or who has been determined to be in need of, such treatment. In some embodiments, the methods also include administering one or more immunotherapies for cancer.

In some embodiments, the present invention provides a method of administering any of the disclosed compositions, including a therapeutically effective amount of the bispecific immunotoxins, described herein to a subject. When administered, the compositions are applied in a therapeutically effective, pharmaceutically acceptable amount as a pharmaceutically acceptable formulation.

As used herein, the term "pharmaceutically acceptable" is given its ordinary meaning. Pharmaceutically acceptable compositions are generally compatible with other materials of the formulation and are not generally deleterious to the subject. Any of the compositions of the present invention may be administered to the subject in a therapeutically effective dose. The dose to the subject may be such that a therapeutically effective amount of one or more other active compounds reaches the active site within the subject, for example via local or systemic administration. A "therapeutically effective" or an "effective" amount or dose, as used herein, means that amount necessary to delay the onset of, inhibit the progression of, halt altogether the onset or progression of, or otherwise achieve a medically desirable result, i.e., that amount which is capable of at least partially preventing, reversing, reducing, decreasing, ameliorating, or otherwise suppressing the particular condition being treated. A therapeutically effective amount can be determined on an individual basis and will be based, at least in part, on consideration of the species of subject's age, sex, size, and health; the composition used, the type of delivery system used; the time of administration relative to the severity of the disease; and whether a single, multiple, or controlled-release dose regiment is employed. A therapeutically effective amount can be determined by one of ordinary skill in the art employing such factors and using no more than routine experimentation.

The terms "treat," "treated," "treating," and the like, when used herein, refer to administration of the systems and methods of the invention to a subject, which may, for example, increase the resistance of the subject to development or further development of cancers, to eliminate or at least control a cancer, and/or to reduce the severity of the cancer. The pharmaceutical preparations of the invention are administered to subjects in effective amounts. When administered to a subject, effective amounts will depend on the particular condition being treated and the desired outcome. A therapeutically effective dose may be determined by those of ordinary skill in the art.

In administering the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration.

The specific concentration may depend upon the particular composition used, as some are more effective than others. The dosage concentration of the composition actually administered is dependent, at least in part, upon the particular disorder being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously affect the subject.

The dosage may be given in some cases at the maximum amount while avoiding or minimizing any potentially detrimental side effects within the subject. The dosage actually administered can be dependent upon factors such as the final concentration desired at the active site, the method of administration to the subject, the efficacy of the composition, the longevity of the composition within the subject, the mode and/or timing of administration, the effect of concurrent treatments (e.g., as in a cocktail), etc. The dose delivered may also depend on conditions associated with the subject and can vary from subject to subject in some cases. For example, the age, sex, weight, size, environment, physical conditions, active site of the cancer or wound, or current state of health of the subject may also influence the dose required and/or the concentration of the composition at the active site. Variations in dosing may occur between different individuals or even within the same individual on different days. These factors are well known to those of ordinary skill in the art and can be addressed with no more than routine experimentation. It is preferred that a maximum dose be used, that is, the highest safe dose according to sound medical judgment.

Administration of a composition of the invention to a subject may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, and route of administration etc.

The systems and methods of the invention can be administered by any method which allows the composition of the invention to reach the target cells, e.g., tumor cells. These methods include, e.g., injection, infusion, deposition, implantation, anal or vaginal supposition, oral ingestion, inhalation, topical administration, or any other method of administration where access to the target cells by the inhibitor is obtained.

In certain embodiments of the invention, the administration of the composition of the invention may be designed so as to result in sequential exposures to the composition over a certain time period, for example, hours, days, weeks, months, or years. This may be accomplished, for example, by repeated administration of a composition of the invention by one of the methods described above, and/or by a sustained or controlled release delivery system in which the composition is delivered over a prolonged period, usually without repeated administrations.

The following description provides specific embodiments. It is to be understood that other embodiments are contemplated and may be made without departing from the scope or spirit of the present invention. The following detailed description, therefore, is not to be taken in a limiting sense. While the present invention is not so limited, an appreciation of various aspects of the invention will be gained through a discussion of the examples provided below, which do not limit the scope of the invention described in the claims.

EXAMPLES

The antibodies used in the Examples below are listed in Table 1.

TABLE 1

Antibodies used in this study

| Antibody Name | Clone | Source | Cat# |
|---|---|---|---|
| Fluorescein-Mouse anti human/rat CCR4 | 205410 | R&D Systems | FAB1567F |
| Mouse IgG2B fluorescein isotype control | 133303 | R&D Systems | IC0041F |
| FITC-mouse anti-human CD25 | BC96 | BioLegend | 302604 |
| FITC-mouse IgG1, κ isotype control | MOPC-21 | BioLegend | 400108 |
| PE-streptavidin | | BioLegend | 405204 |
| Propidium Iodide | | Sigma | 81845 |
| 7-Aminoactinomycin D (7-AAD) | | Sigma | A9400 |

Human $CD25^+CCR4^+$ T-cell lymphoma cell line Hut 102/6TG (Williams D P, et al., *J. Biol Chem* 265, 20673-20677, 1990) were used in the examples.

Human T lymphocyte cell line, Jurkat, clone E6-1 (ATCC TIB-152); human $CCR4^+$ acute lymphoblastic leukemia cell line CCRF-CEM (ATCC CCL-119); human $CD25^+$ lymphoma cell line, SR (ATCC CRL-2262) were also used in the examples.

Protein expression in *Pichia pastoris* and subsequent purifications were performed as previously described (Wang et al., 2011; Example 1 and Peraino, J S et al., *J. Immunol. Methods* 398-399, 33-43, 2013). Western blot analysis, binding affinity and specificity analysis by flow cytometry and Kd determination were all performed as previously described (Example 1 and Peraino et al., 2013) using a human CD25+ T-cell lymphoma cell line HUT 102/6TG (William et al., 1990). DT390 and human IL-2 were used as controls for all in vitro functional analysis. These products were also expressed in the yeast *Pichia pastoris* system.

In vitro efficacy of the immunotoxins against the tumor cell line was assessed using CellTiter-Glo® Luminescent Cell Viability Assay (Promega, cat #G7571) as described previously (Zheng, Q. et al., *Mol. Oncol.* 11, 584-594, 2017). The cell viability assay measures the luminescence produced as a result of ATP production from metabolically active cells. The increasing concentrations of cytotoxic immunotoxins lead to cells death and a corresponding reduction in ATP related fluorescence. The luminescence signals were recorded using Wallac Victor2 1420 multilabel counter (Perkin Elmer).

Human $CD25^+$ $CCR4^+$ CTCL Hut102/6TG tumor-bearing immunodeficient NSG mouse model was employed to assess the in vivo efficacy of the immunotoxins as described (Wang et al., 2015). Breeding pairs of immunodeficient NSG mice were purchased from Jackson laboratories (Bar Harbor, Maine) and bred in our rodent barrier facilities. The NSG mice were divided into the following groups: 1) C21 immunotoxin group as a negative control (a non-related diphtheria toxin-based immunotoxin) (n=13); 2) human IL2 fusion toxin group (n=12); 3) single-chain foldback diabody anti-human CCR4 immunotoxin group (n=12); 4) IL2-CCR4 bispecific immunotoxin group (n=12); 5) CCR4-IL2 bispecific immunotoxin group (n=14). All animals were IV injected at day 0 with 10 million human $CD25^+CCR4^+$ Hut102/6TG tumor cells via the tail vein. The immunotoxin was IP injected from day 4 on at $8.3\times10^{-10}$ moles/kg, once daily for 10 consecutive days. The injected animals were observed daily for signs and symptoms of illness and scored at least twice weekly based on the parameters as previously reported by our lab (Peraino et al., 2013; Wang et al., 2015). The animals were humanely euthanized when the score exceeded the limit or the animal lost more than 15% of its pre-injection body weight.

Liver necropsy specimens were obtained surgically on day 21 after animal euthanasia. Tissues were fixed in 10% formalin and embedded in paraffin and subsequently sectioned. Tissues were stained with hematoxylin and eosin for routine light microscopy. Slides were digitalized by Aperio Scanscope (Leica), and images were analyzed at 2× and 30× with Aperio ImageScope software (Leica).

The survival curve comparison was performed using Log-rank (Mantel-Cox) test of GraphPad Prism 7 (GraphPad software Inc. San Diego, CA). $IC_{50}$ was determined using nonlinear regression of Prism.

Example 1

Figure 3:
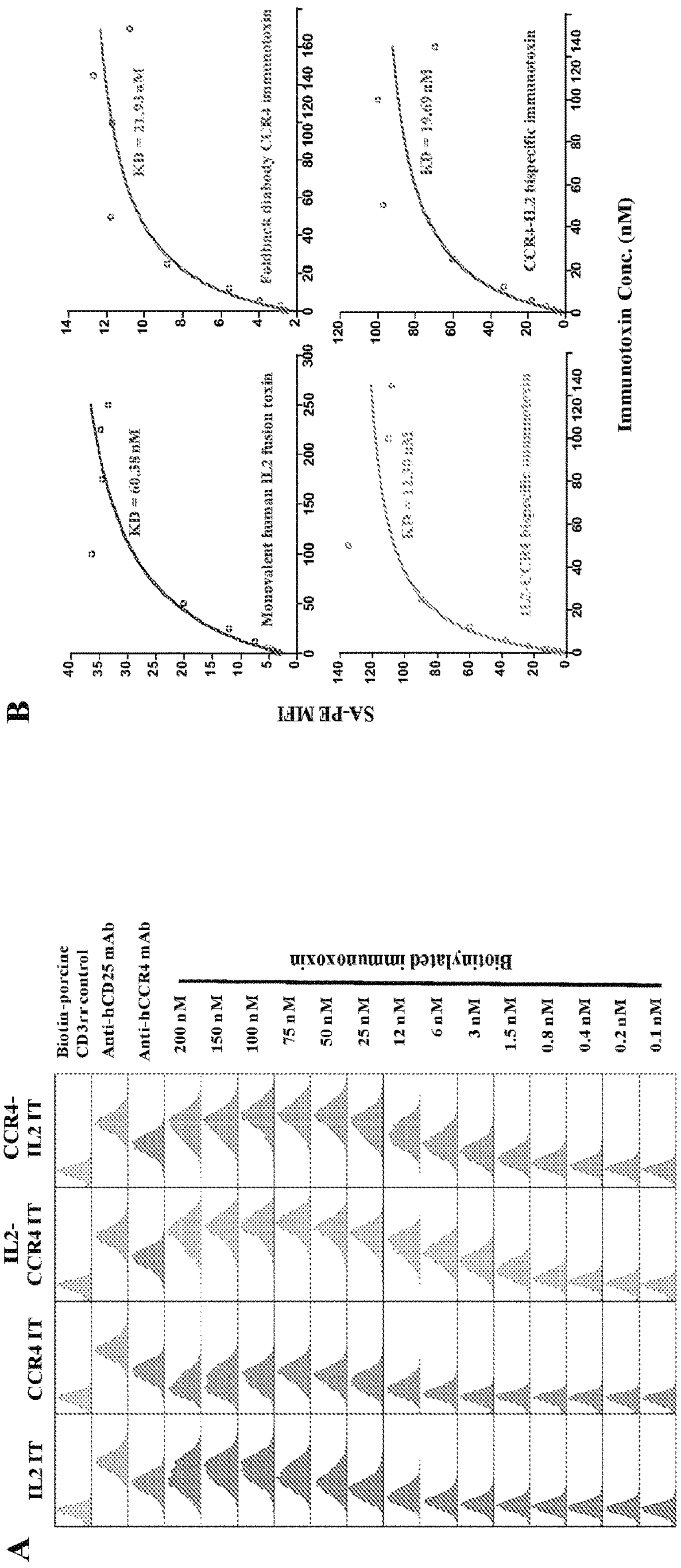
FIG. 3 is A) Flow cytometry binding affinity analysis of the biotinylated 1) IL2 fusion toxin alone; 2) CCR4 immunotoxin alone; 3) IL2-CCR4 bispecific immunotoxin; 4) CCR4-IL2 bispecific immunotoxin to human $CD25^{+}CCR4^{+}$ Hut102/6TG cells. Fluorescein-Mouse anti human/rat CCR4 mAb and FITC-mouse anti-human CD25 mAb were used as positive controls. Biotin-labeled porcine CD3-εγ (Peraino, J S et al., *Cell. Immunol.* 276, 162-167, 2012) was included as a negative control for background due to protein biotinylation. The data are representative of three individual experiments. B) $K_D$ determination using flow cytometry and nonlinear least squares fit. MFI was plotted over a wide range of concentrations of biotinylated 1) IL2 fusion toxin alone; 2) CCR4 immunotoxin alone; 3) IL2-CCR4 bispecific immunotoxin; 4) CCR4-IL2 bispecific immunotoxin. The accompanying least-squares fits are shown based on the hyperbolic equation $y=m_1+m_2*m_0/(m_3+m_0)$ where y=MFI at the given biotinylated immunotoxin concentration, $m_0$=biotinylated immunotoxin concentration, $m_1$=MFI of zero biotinylated immunotoxin control, $m_2$=MFI at saturation and $m_3=K_D$.
Figure 5:
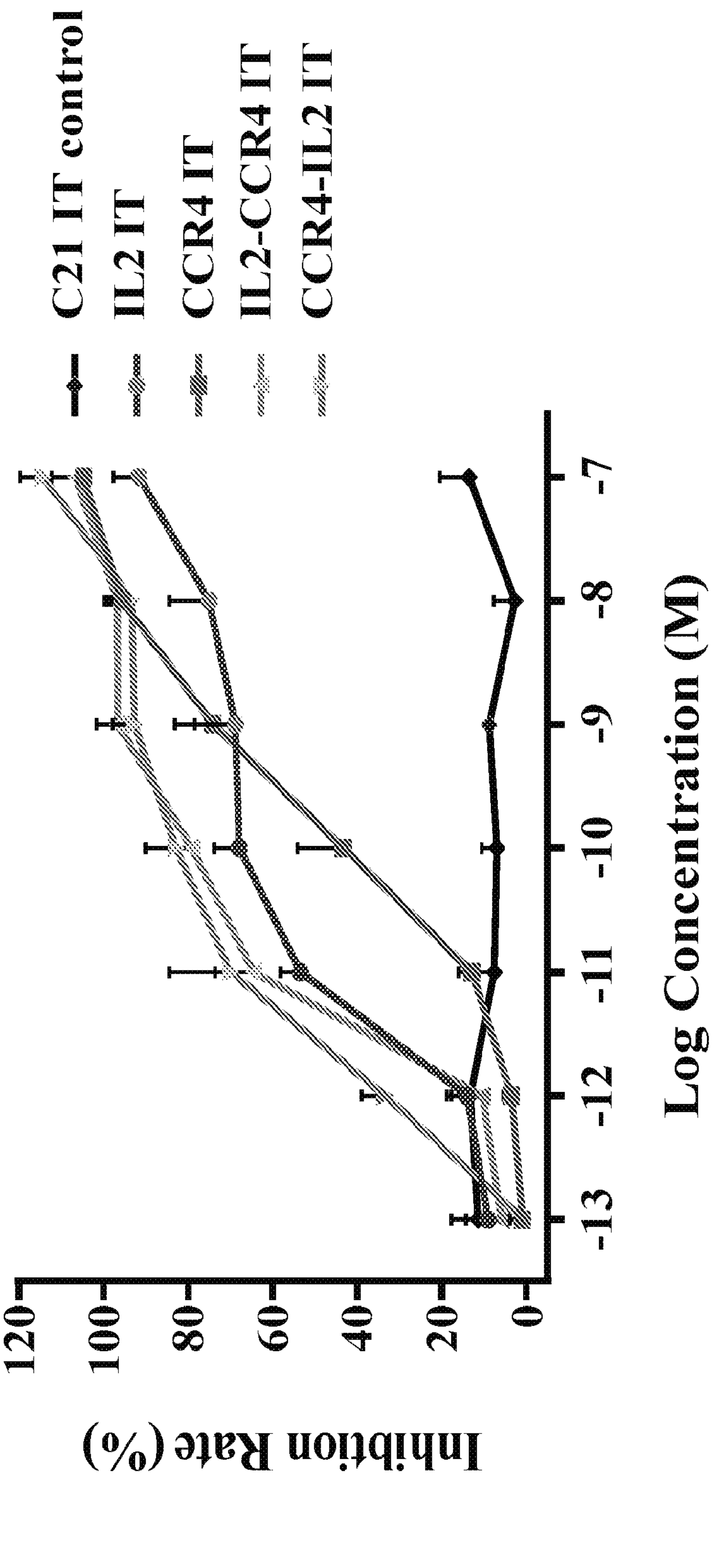
FIG. 5 is in vitro efficacy analysis of the bispecific immunotoxins using CellTiter-Glo® Luminescent Cell Viability Assay (Promega, cat #G7571) to human $CD25^{+}$ $CCR4^{+}$ T-cell lymphoma cell line Hut102/6TG. 1) C21 immunotoxin as negative control (C21 IT control); 2) IL2 fusion toxin alone (IL2 IT); 3) CCR4 immunotoxin alone (CCR4 IT); 4) IL2-CCR4 bispecific immunotoxin (IL2-CCR4 IT); 5) CCR4-IL2 bispecific immunotoxin (CCR4-IL2). Y-axis: inhibition rate of the cell viability by determining the number of viable cells based on the quantification of the ATP present. X-axis: plated immunotoxin concentration. Cycloheximide (1.25 mg/mL) was used as a positive control. The negative control contained cells without immunotoxin. Data are representative of multiple assays.
Figure 7:
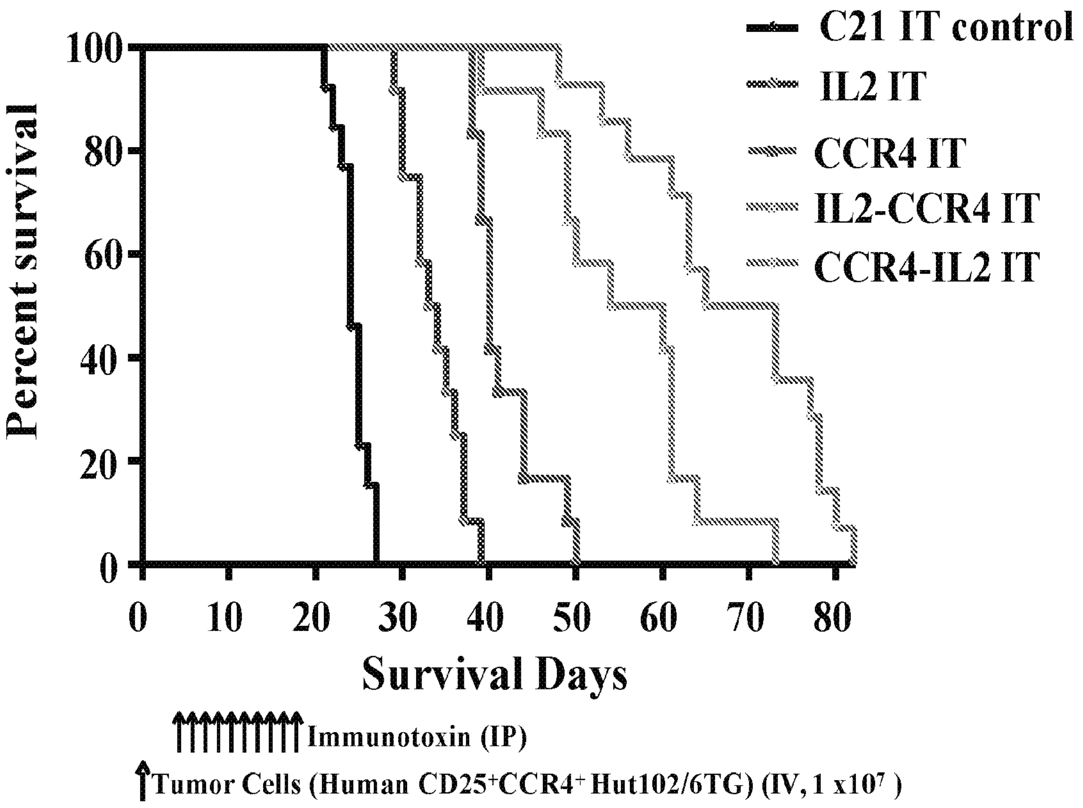
FIG. 7 is in vivo efficacy assessment of the bispecific immunotoxins. NSG mice were IV injected with $1.0\times10^7$ human $CD25^+CCR4^+$ Hut102/6TG cells on day 0 and treated from day 4 on with the imunotoxin (IP injection) at $8.3\times10^{-10}$ moles/kg daily for 10 consecutive days. 1) C21 immunotoxin control group (a non-related DT390-based immunotoxin as negative control) (n=13, C21 IT control) with a median survival time of 24 days; 2) IL2 fusion toxin alone group (n=12, IL2 IT) with a median survival time of 33.5 days; 3) CCR4 immunotoxin alone group (n=12, CCR4 IT) with median survival time of 40 days; 4) IL2-CCR4 bispecific immunotoxin group (n=12, IL2-CCR4 IT) with a median survival time of 57 days; 5) CCR4-IL2 bispecific immunotoxin group (n=14, CCR4-IL2 IT) with a median survival time of 69 days. The schedule of the immunotoxin and tumor cell injection is pictured in the schematic below the survival curve. The vertical arrows indicate the days on which the tumor cells or the immunotoxins were injected. The data are pooled from two separate experiments.

Analysis of the Efficacy of CCR4 Immunotoxin Compared to IL2 Fusion Toxin to Human $CD25^+CCR4^+$ CTCL Hut102/6TG The binding affinity of the CCR4 immunotoxin to human $CD25^+CCR4^+$ CTCL Hut102/6TG was analyzed using flow cytometry. The results showed that biotinylated CCR4 immunotoxin bound to human $CD25^+CCR4^+$ CTCL Hut102/6TG in a dose-dependent manner (FIG. 3A) with a Kd value of 21.93 nM (FIG. 3B), which was stronger than that of IL2 fusion toxin with Kd value of 60.38 nM (FIG. 3B). In vitro efficacy comparison of the CCR4 immunotoxin versus IL2 fusion toxin to human $CD25^+CCR4^+$ CTCL Hut102/6TG was performed using luminescent cell viability assay. As shown in FIG. 5 and Table 2, the IL2 fusion toxin ($IC_{50}1=\times10^{-10.5}$ M) was more effective than CCR4 immunotoxin ($IC_{50}=1\times10^{-9.8}$ M) to human $CD25^+CCR4^+$ CTCL Hut102/6TG. In vivo efficacy comparison analysis demonstrated that CCR4 immunotoxin prolonged human $CD25^+$ $CCR4^+$ Hut102/6TG-bearing immunodeficient NSG mouse survival significantly more than IL2 fusion toxin with median survival days of 40 versus 33.5 (FIG. 7, Tables 2 and 3).

TABLE 2

In vitro and in vivo efficacy summary of the tested immunotoxins in this study

| | C21 IT | IL2 IT | CCR4 IT | IL2-CCR4 IT | CCR4-IL2 IT |
|---|---|---|---|---|---|
| $IC_{50}$ (M) | | $10^{-10.5}$ | $10^{-9.8}$ | $10^{-11.2}$ | $10^{-11.5}$ |
| Median Survival Days | 24 | 33.5 | 40 | 57 | 69 |

TABLE 3

Survival curve log-rank (Mantel-Cox) test

| | C21 IT | IL2 IT | CCR4 IT | IL2-CCR4 IT | CCR4-IL2 IT |
|---|---|---|---|---|---|
| C21 IT | — | *** | *** | *** | *** |
| IL2 IT | *** | — | *** | *** | *** |
| CCR4 IT | *** | *** | — | *** | *** |
| IL2-CCR4 IT | *** | *** | *** | — | ** |
| CCR4-IL2 IT | *** | *** | *** | ** | — |

$p \leq 0.01$; *$p \leq 0.001$

Example 2

Expression and Purification of the IL2-CCR4 and CCR4-IL2 Bispecific Immunotoxins Two bispecific immunotoxins were constructed: 1) IL2-CCR4 bispecific immunotoxin; and 2) CCR4-IL2 bispecific immunotoxin. The bivalent anti-human CCR4 immunotoxin (Wang et al., 2015) was used as a template to construct the IL2-CCR4 or CCR4-IL2 bispecific immunotoxin by replacing the first or second anti-human CCR4 scFv using human IL2, as shown in FIG. 1, and described below.

IL2-CCR4 bispecific immunotoxin construction: bivalent anti-human CCR4 immunotoxin [DT390-BiscFv(1567)-6×His] in pwPICZalpha (Wang et al., 2015) was digested using NcoI and BamHI and separated with DNA agarose gel. The large band (~4.35 kb) was cut out and extracted as vector. Bivalent human IL2 fusion toxin (DT390-Bi-hIL2-6×His) developed previously (Peraino et al, 2014) was digested using NcoI and BamHI. The digestion mixture was separated with DNA agarose gel. The human IL2 (~459 bp) carrying NcoI and BamHI was cut out and extracted as insert. The prepared human IL2 insert carrying NcoI and BamHI was cloned into the prepared pwPICZalpha-DT390-scFv(1567) vector (NcoI-BamHI digested) yielding the IL2-CCR4 bispecific immunotoxin DNA construct (FIG. 1). Alternate vectors are available, including from Invitrogen.

CCR4-IL2 bispecific immunotoxin construction: bivalent anti-human CCR4 immunotoxin [DT390-BiscFv(1567)-6×His] in pwPICZalpha (Wang et al., 2015) was digested using BamHI and EcoRI and separated with DNA agarose gel. The large band (~4.35 kb) were cut out and extracted as vector. Bivalent human IL-2 fusion toxin in pwPICZalpha (DT390-Bi-hIL2-6×His) (Peraino et al., 2014) was digested using BamHI and EcoRI. The digestion mixture was separated with DNA agarose gel. The human IL2 (~459 bp) carrying BamHI and EcoRI was cut out and extracted as insert. The prepared human IL2 insert carrying BamHI and EcoRI was cloned into prepared pwPICZalpha-DT390-scFv(1567) vector (BamHI-EcoRI digested) yielding the CCR4-IL2 bispecific immunotoxin DNA construct (FIG. 1). Alternate vectors are available, including from Invitrogen.

The linearized immunotoxin DNA constructs (IL2-CCR4 bispecific immunotoxin and the CCR4-IL2 bispecific immunotoxin) were transformed into diphtheria toxin resistant yeast *Pichia pastoris* strain (Liu et al., 2003) for expression and purification, as previously described (Wang et al., 2015). The strain was obtained by Angimmune.

IL2 fusion toxin (Peraino et al., 2014), CCR4 immunotoxin (Wang et al., 2015) and C21 immunotoxin (truncated diphtheria toxin DT390-based unrelated immunotoxin) were also expressed and purified in our lab using the same diphtheria toxin resistant yeast *Pichia pastoris* expression system. Western blot analysis, flow cytometry binding affinity analysis and Kd determination were all performed as previously described (Peraino et al., 2014; Wang et al., 2015). Methods for the yeast expression system are known (e.g., U.S. Pat. No. 7,892,786).

Figure 2:
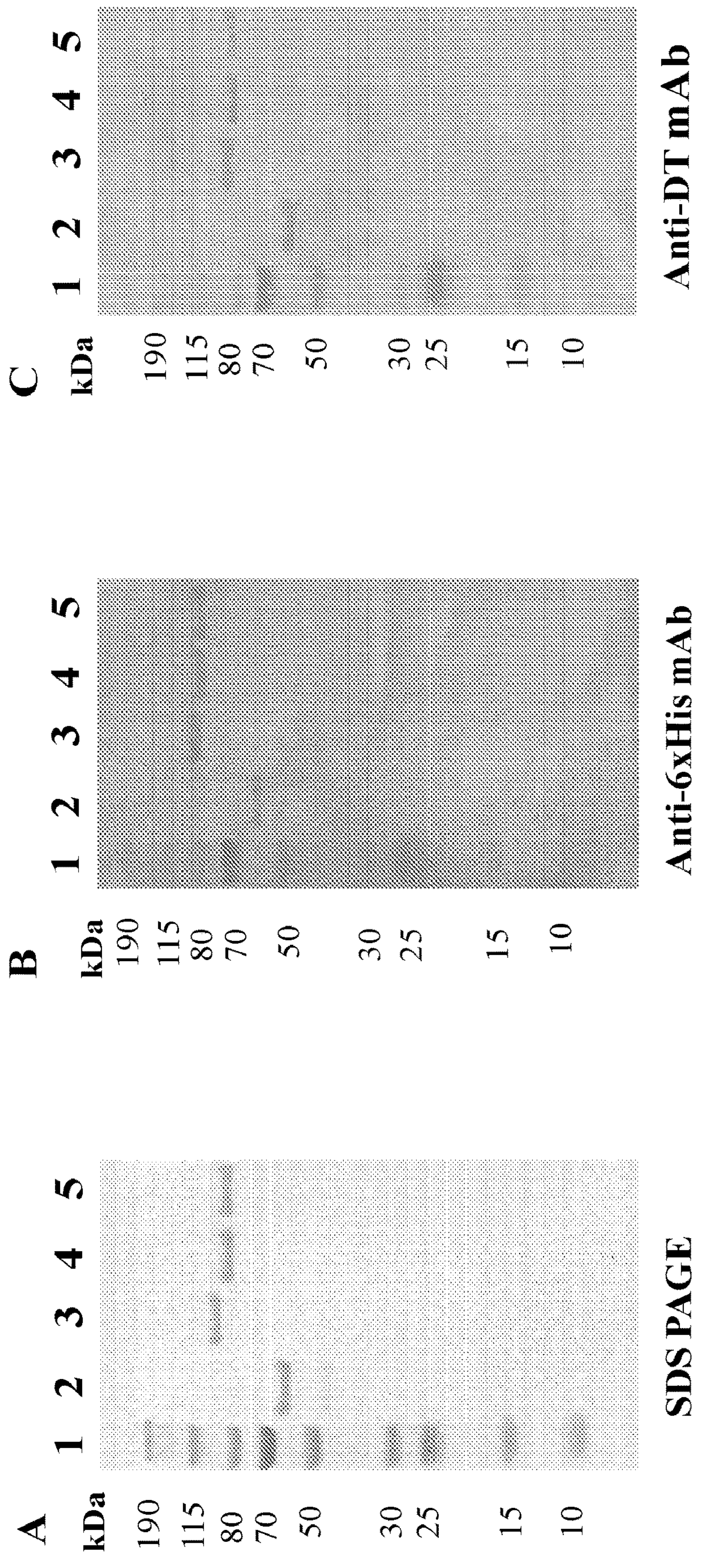
FIG. 2 is an SDS-PAGE and Western blot analysis of the bispecific immunotoxins. A) SDS-PAGE analysis (4-12% NuPAGE, Invitrogen); The lower molecular weight weak band (~45 kDa) in lane 2 is the broken down product of the IL2 fusion toxin; B) Western blot analysis using a mouse anti-His mAb (clone #: 4A12E4, Invitrogen); C) Western blot analysis using a mouse anti-diphtheria toxin mAb (clone #3B6, Meridian). Lane 1: Protein marker; Lane 2: monovalent human IL2 fusion toxin (59 kDa); Lane 3: single-chain foldback diabody anti-human CCR4 immunotoxin (96 kDa); Lane 4: IL2-CCR4 bispecific immunotoxin (86 kDa); Lane 5: CCR4-IL2 bispecific immunotoxin (86 kDa).

The final purification yield is ~7 mg per liter of the original harvested supernatant. SDS-PAGE and Western Blot analysis demonstrated that the two versions of the bispecific immunotoxin were successfully expressed and purified with expected molecular weight of ~86 kDa (FIG. 2A-C).

Example 3

Analysis of In Vitro Binding Affinity and Efficacy of Bispecific Immunotoxins Compared to Monospecific Immunotoxins The binding affinity of the biotinylated IL2-CCR4 or CCR4-IL2 bispecific immunotoxin to human $CD25^+CCR4^+$ Hut102/6TG was analyzed using flow cytometry and found to have a Kd value of 12.3 nM for IL2-CCR4 immunotoxin and 19.69 nM for CCR4-IL2 immunotoxin (FIG. 3A-B). The bispecific immunotoxins bound more strongly than IL2 fusion toxin and CCR4 immunotoxin individually (FIG. 3A-B). The in vitro efficacy was assessed using luminescent based cell viability assay. The bispecific immunotoxins ($IC_{50}=10^{-11.2}$ M for IL2-CCR4 immunotoxin and $IC_{50}=10^{-11.5}$ M for CCR4-IL2 immunotoxin) were also more potent than either CCR4 immunotoxin ($IC_{50}=10^{-9.8}$ M) or IL2 fusion toxin alone ($IC_{50}=10^{-10.5}$ M) (FIG. 5 and Table 2).

Figure 4A:
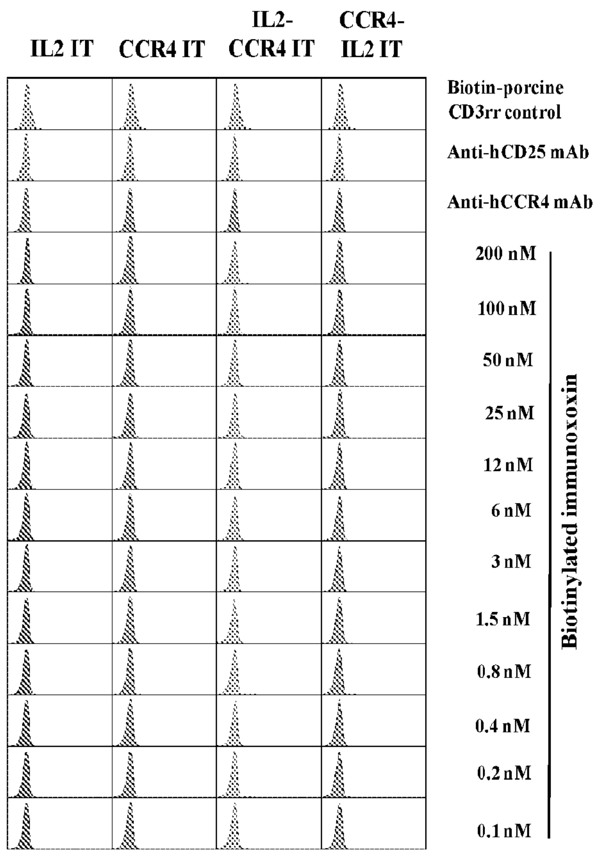
FIGS. 4A-4D is flow cytometry binding affinity analysis with data shown in panels. The left panel provides: Flow cytometry binding affinity analysis of the biotinylated IL2-CCR4 or CCR4-IL2 bispecific immunotoxins to A) human CD25 and CCR4 double negative Jurkat cell line; B) human CD25 single positive SR cell line; C-D) human CCR4 single positive CCL-119 cell line. Biotinylated IL2 fusion toxin alone, foldback-diabody anti-human CCR4 immunotoxin alone (CCR4 IT) and monovalent anti-human CCR4 immunotoxin alone (mono CCR4 IT) were included as controls. Fluorescein-mouse anti-human/rat CCR4 mAb and FITC-mouse anti-human CD25 mAb were used as positive controls. Biotin-labeled porcine CD3-εγ (Peraino et al., 2012) was included as a negative control for background due to protein biotinylation. The data are representative of three individual experiments. The right panel (in FIG. 4B-4D) provides: $K_D$ determination using flow cytometry and nonlinear regression, saturation binding equation by GraphPad Prism. MFI was plotted over a wide range of concentrations of the biotinylated 1) IL2 fusion toxin alone; 2) foldback diabody anti-human CCR4 immunotoxin alone (CCR4 IT); 3) IL2-CCR4 bispecific immunotoxin; 4) CCR4-IL2 bispecific immunotoxin; 5) monovalent anti-human CCR4 immunotoxin alone (Mono CCR4 IT, only in FIG. 4D). The nonlinear regression fit shown was based the equation $Y=Bmax*X/(K_D+X)$, where Y=MFI at the given biotinylated immunotoxin concentration after subtracting off the background; X=biotinylated immunotoxin concentration; Bmax=the maximum specific binding in the same units as Y.
Figure 4B:
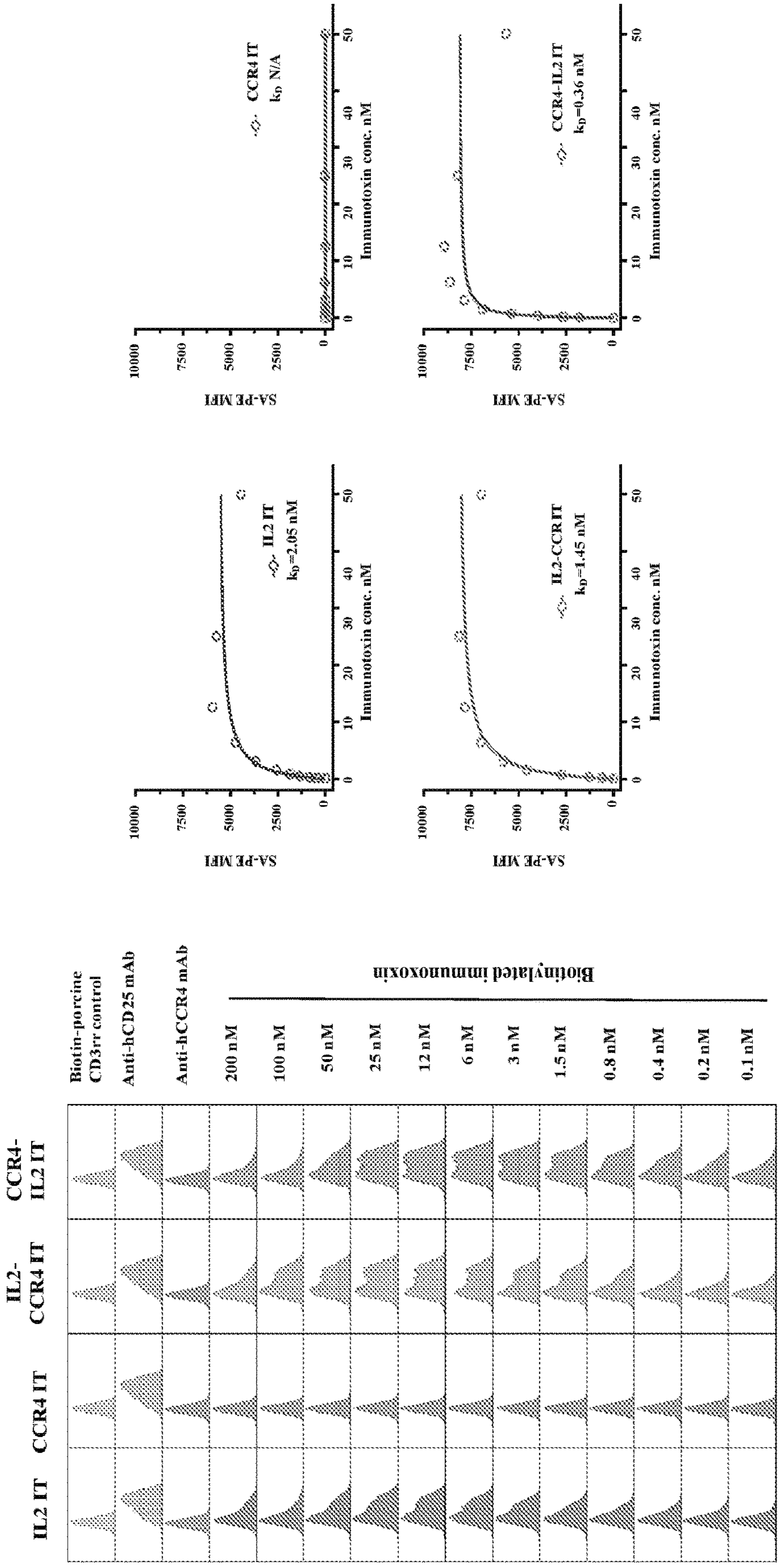
Figure 4C:
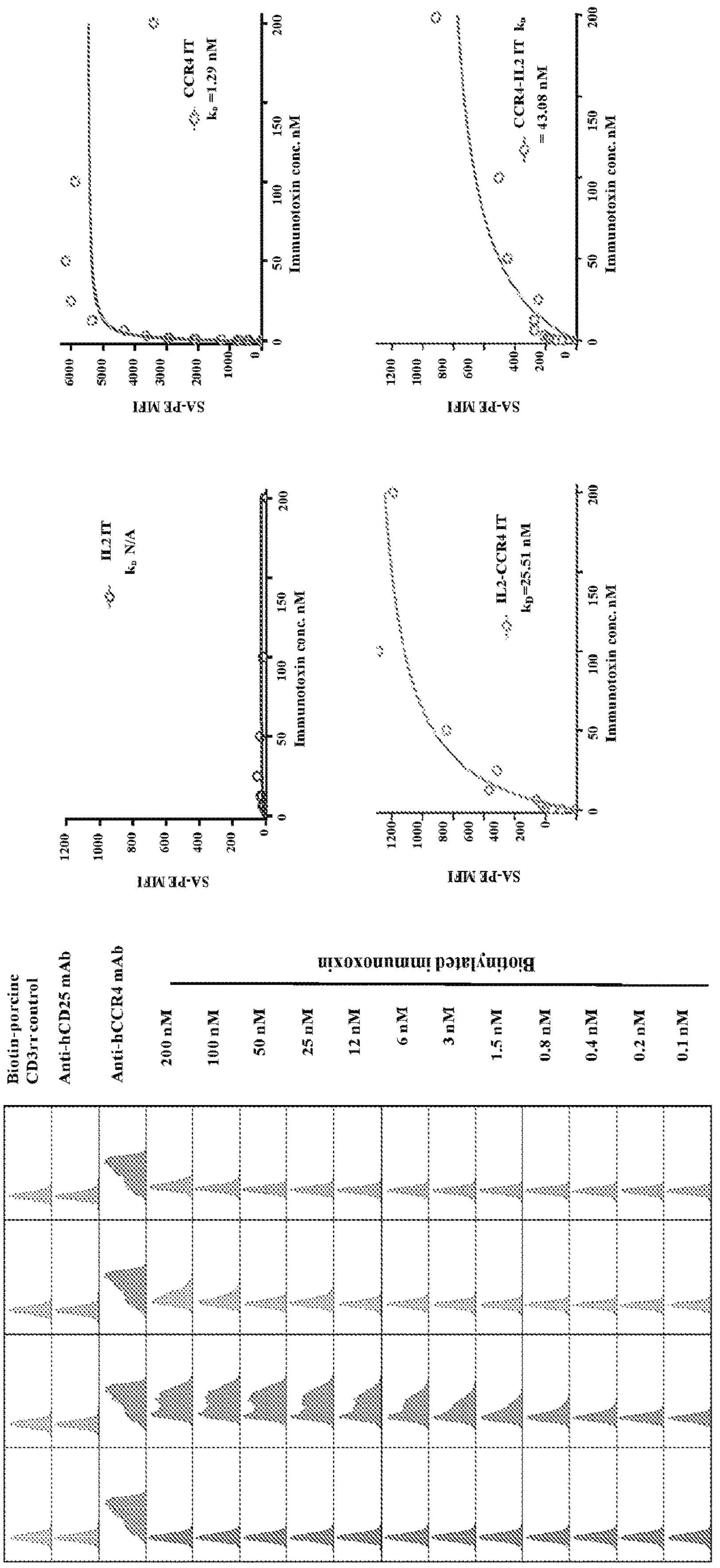
Figure 4D:
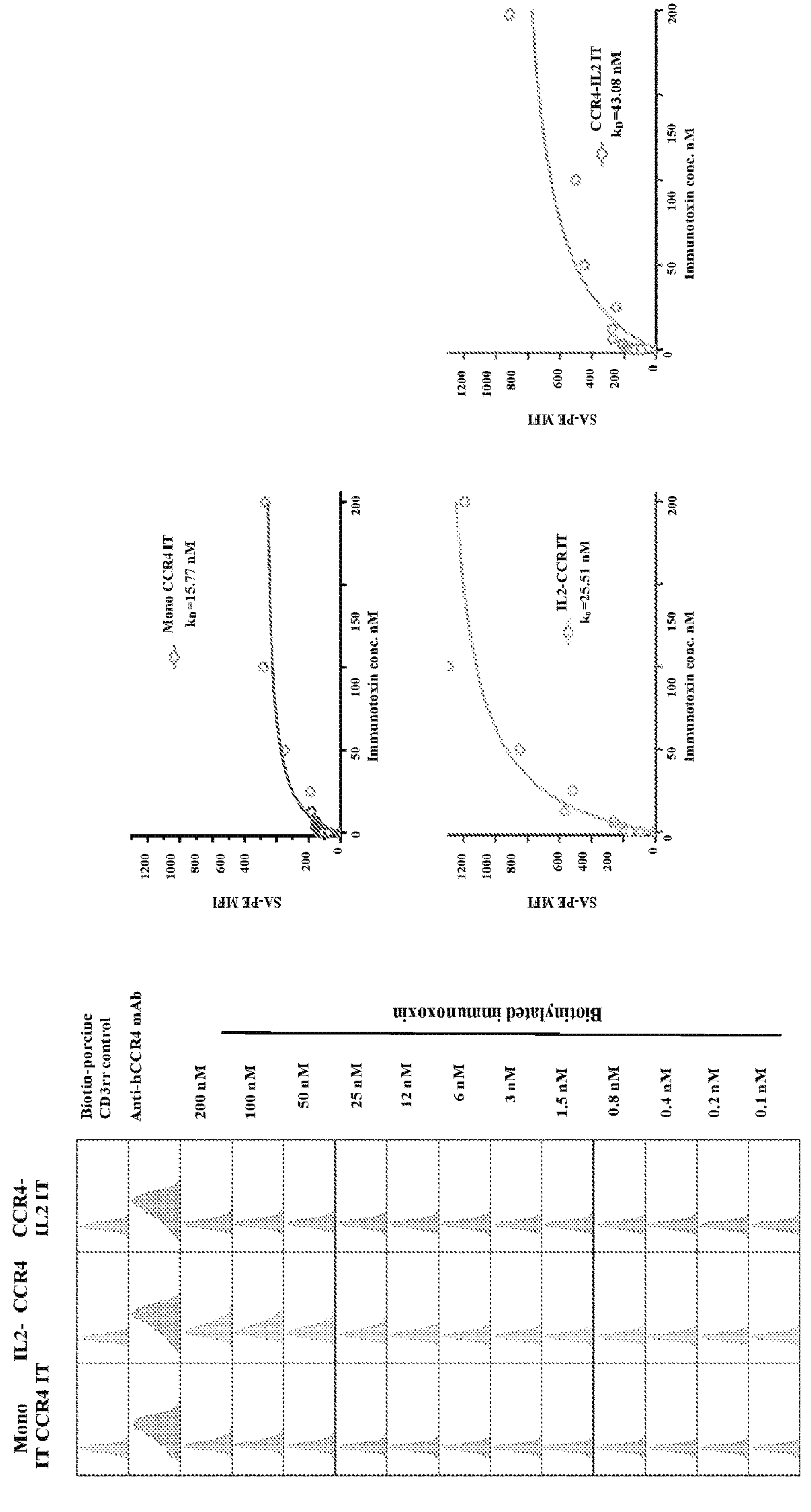
Figure 6A:
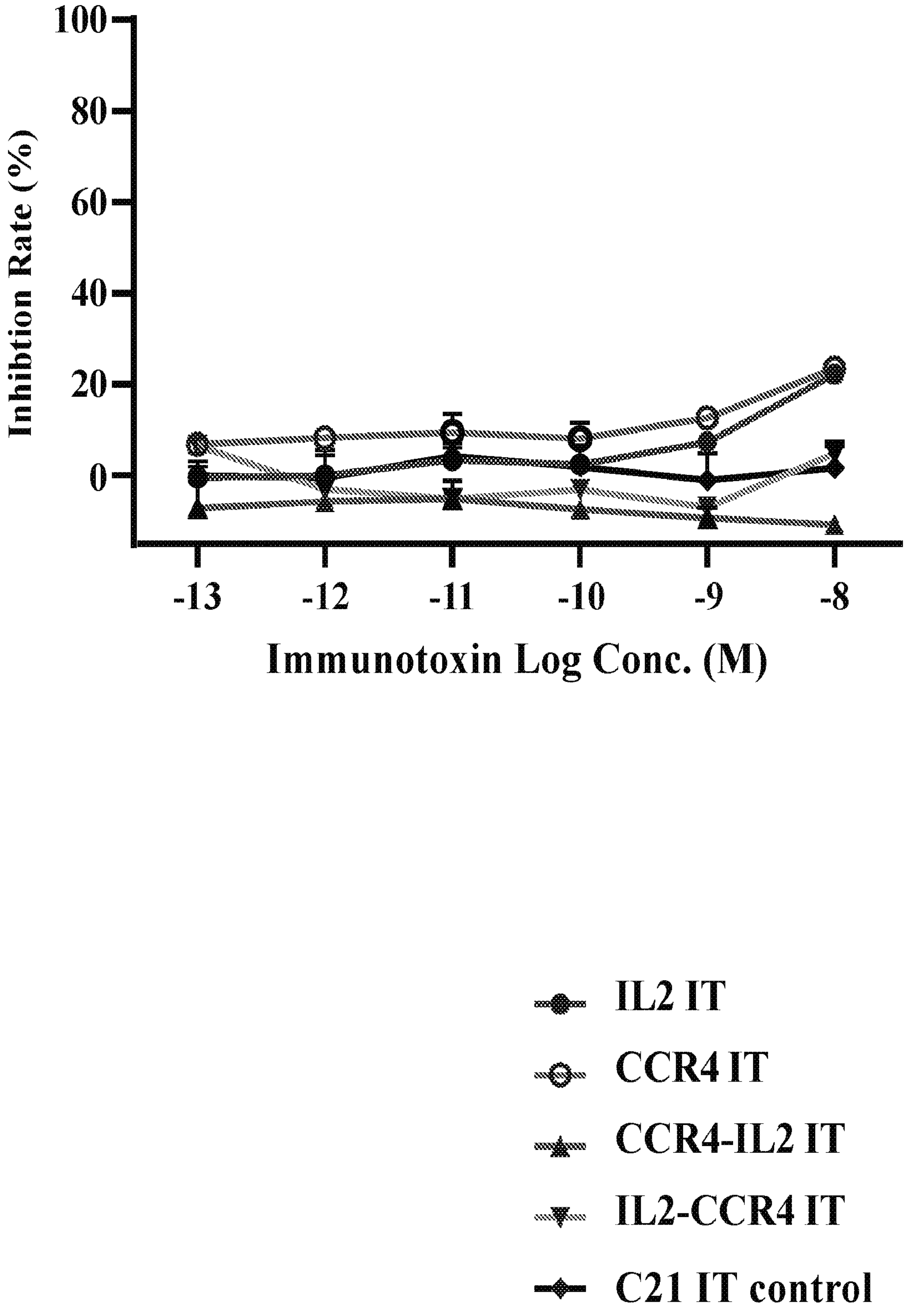
FIGS. 6A-6D reports an in vitro efficacy analysis of the bispecific immunotoxins using CellTiter-Glo® Luminescent Cell Viability Assay (Promega, cat #G7571) to A) human CD25 and CCR4 double negative Jurkat cell line; B) human CD25 single positive SR cell line; C and D) human CCR4 single positive CCL-119 cell line. C21 immunotoxin as negative control (FIG. 6A-C, C21 IT control); IL2 fusion toxin alone (FIG. 6A-C, IL2 IT); foldback diabody anti-human CCR4 immunotoxin alone (CCR4 IT) (FIG. 6A-C, CCR4 IT); IL2-CCR4 bispecific immunotoxin (FIG. 6A-D, IL2-CCR4 IT); CCR4-IL2 bispecific immunotoxin (FIG. 6A-D, CCR4-IL2 IT); monovalent anti-human CCR4 immunotoxin (mono CCR4 IT) (FIG. 6D, Mono CCR4 IT). Y-axis: inhibition rate of the cell viability by determining the number of viable cells based on the quantification of the ATP present. X-axis: plated immunotoxin concentration. Cycloheximide (1.25 mg/mL) was used as a positive control. The negative control contained cells without immunotoxin. Data are representative of multiple assays.
Figure 6B:
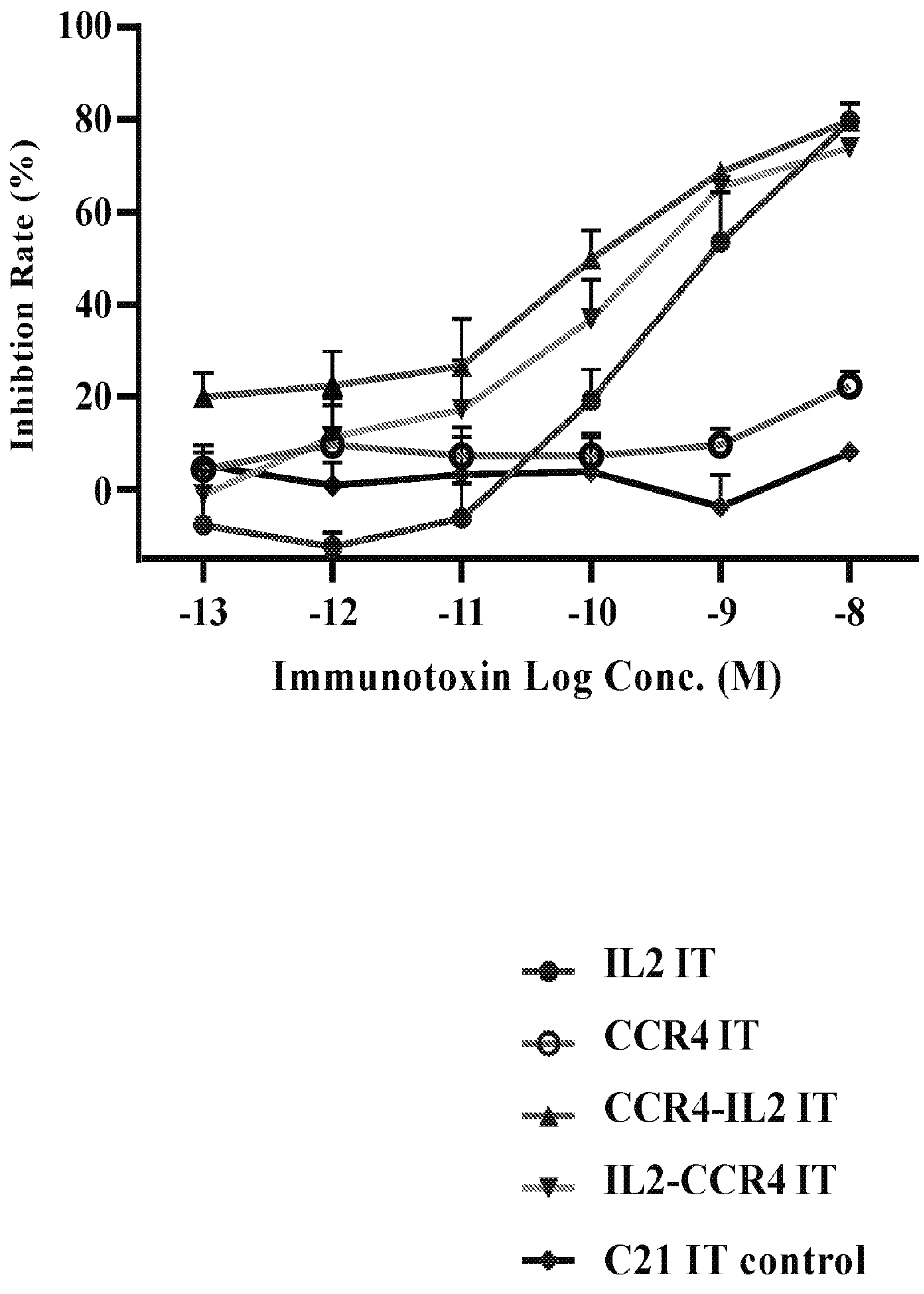
Figure 6C:
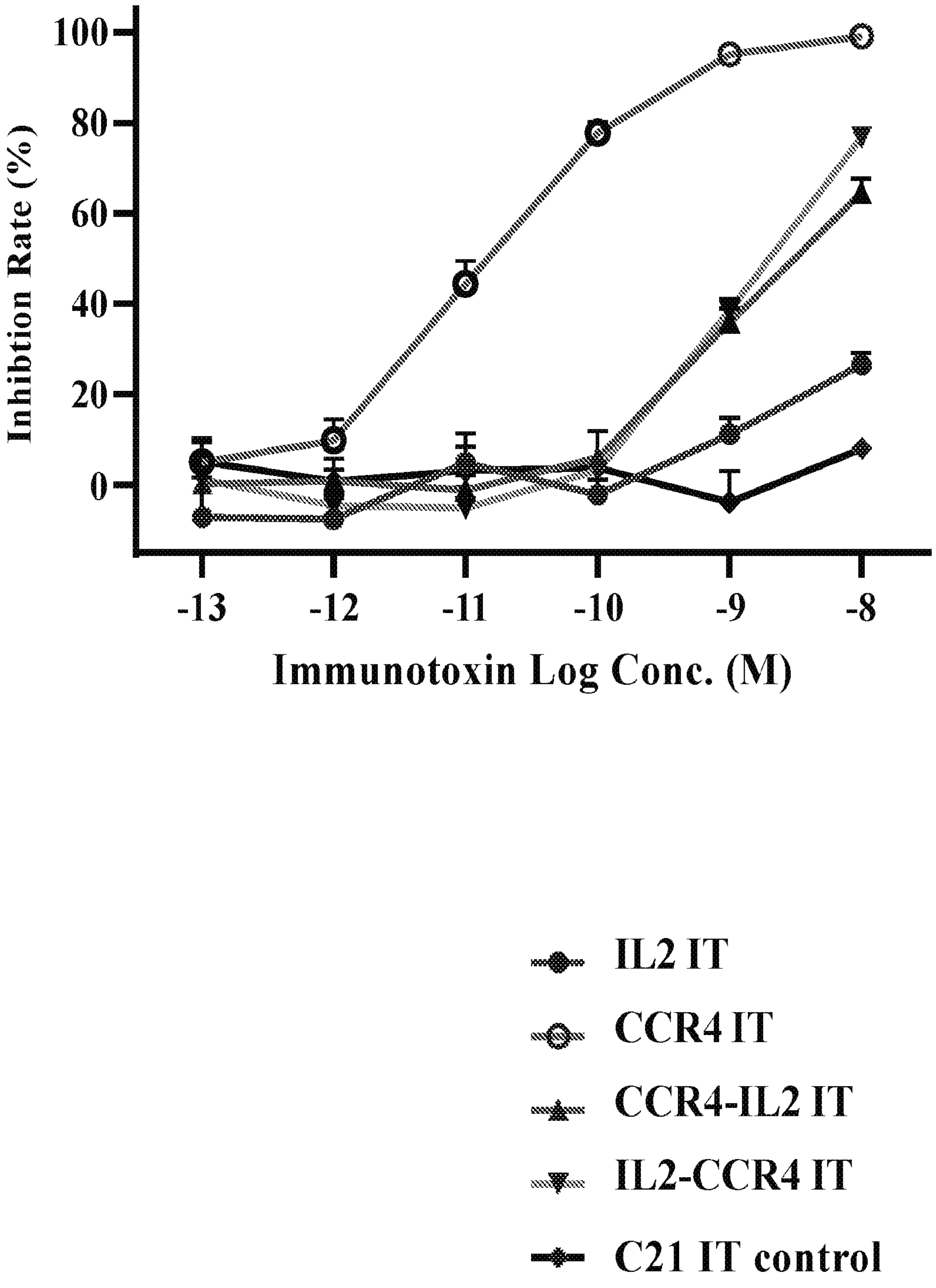
Figure 6D:
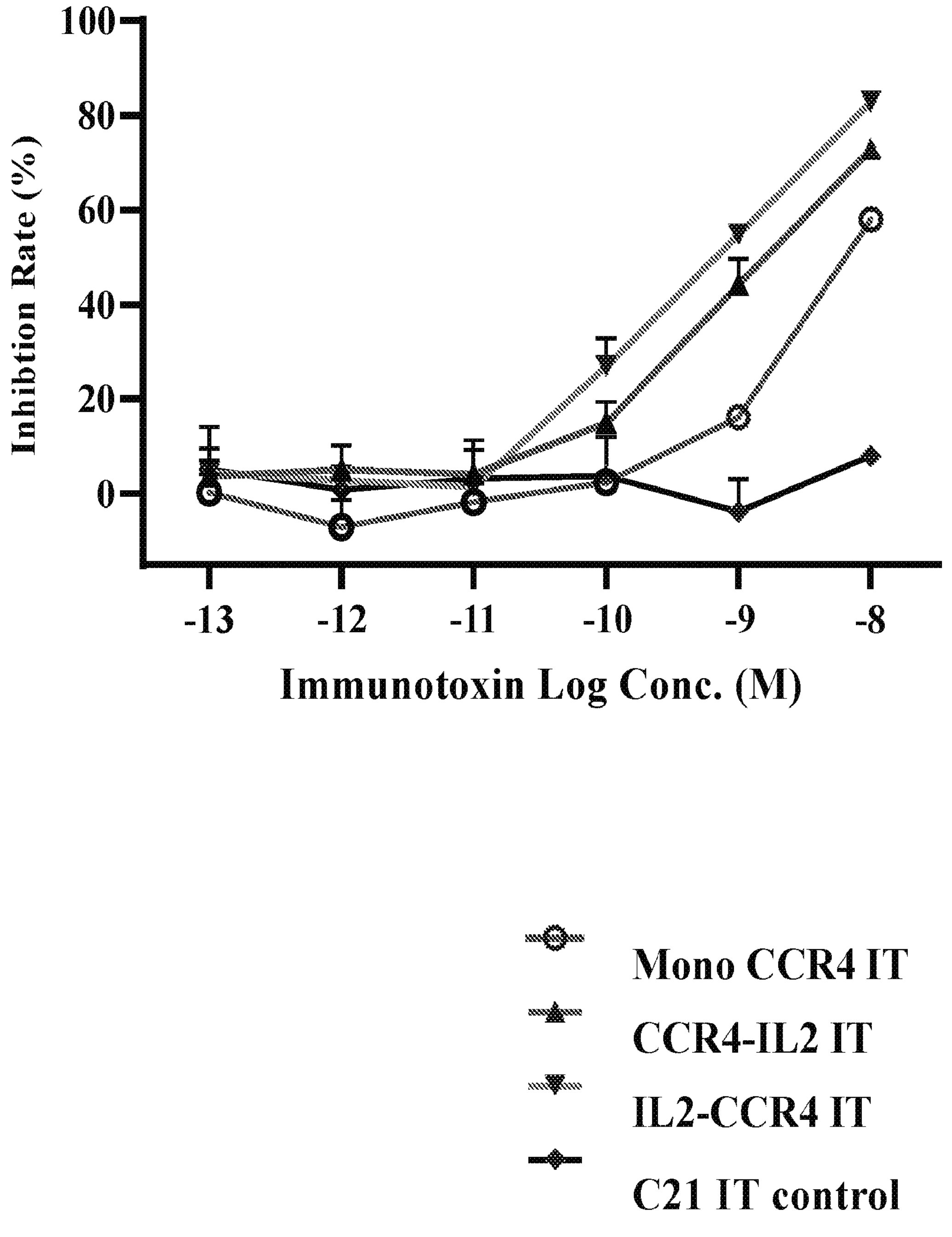

To further characterize the bispecific immunotoxins, in vitro flow cytometry binding affinity and luminescent based cell viability analysis of the bispecific immunotoxins was performed to 1) human CD25 and CCR4 double negative Jurkat cell line; 2) human CD25 single positive SR cell line; and 3) human CCR4 single positive CCL-119 cell line. As shown in FIGS. 4A and 6A, no in vitro binding or efficacy were observed for the bispecific immunotoxins to CD25 and CCR4 double negative Jurkat cells. As shown in FIGS. 4B and 6B, higher in vitro binding and efficacy were observed for the bispecific immunotoxins to CD25 single positive SR cells than that of the IL2 fusion toxin alone. As shown in FIGS. 4C and 4D, weak in vitro binding and efficacy were observed for the bispecific immunotoxins to CCR4 single positive CCL-119 cells. The binding affinity and efficacy were significantly weaker than that of the foldback diabody anti-human CCR4 immunotoxin (CCR4 IT) (FIGS. 4C and 6C, Wang et al., 2015) and comparable to that of the monovalent anti-human CCR4 immunotoxin (Mono CCR4 IT) (FIGS. 4D and 6D, Wang et al., 2015). Without being limited to any one theory, this may be because the bispecific immunotoxins only contain one anti-human CCR4 scFv. Taken together, the bispecific immunotoxins were more effective than IL2 fusion toxin or CCR4 immunotoxin alone to CCR4 and CD25 double positive or CD25 single positive cells, but less effective than foldback diabody anti-human CCR4 immunotoxin alone to CCR4 single positive cells. Foldback diabody anti-human CCR4 immunotoxin (Wang et al., 2015) is still more effective than the bispecific immunotoxins for targeting CCR4 single positive cells.

Example 4

Figure 8:
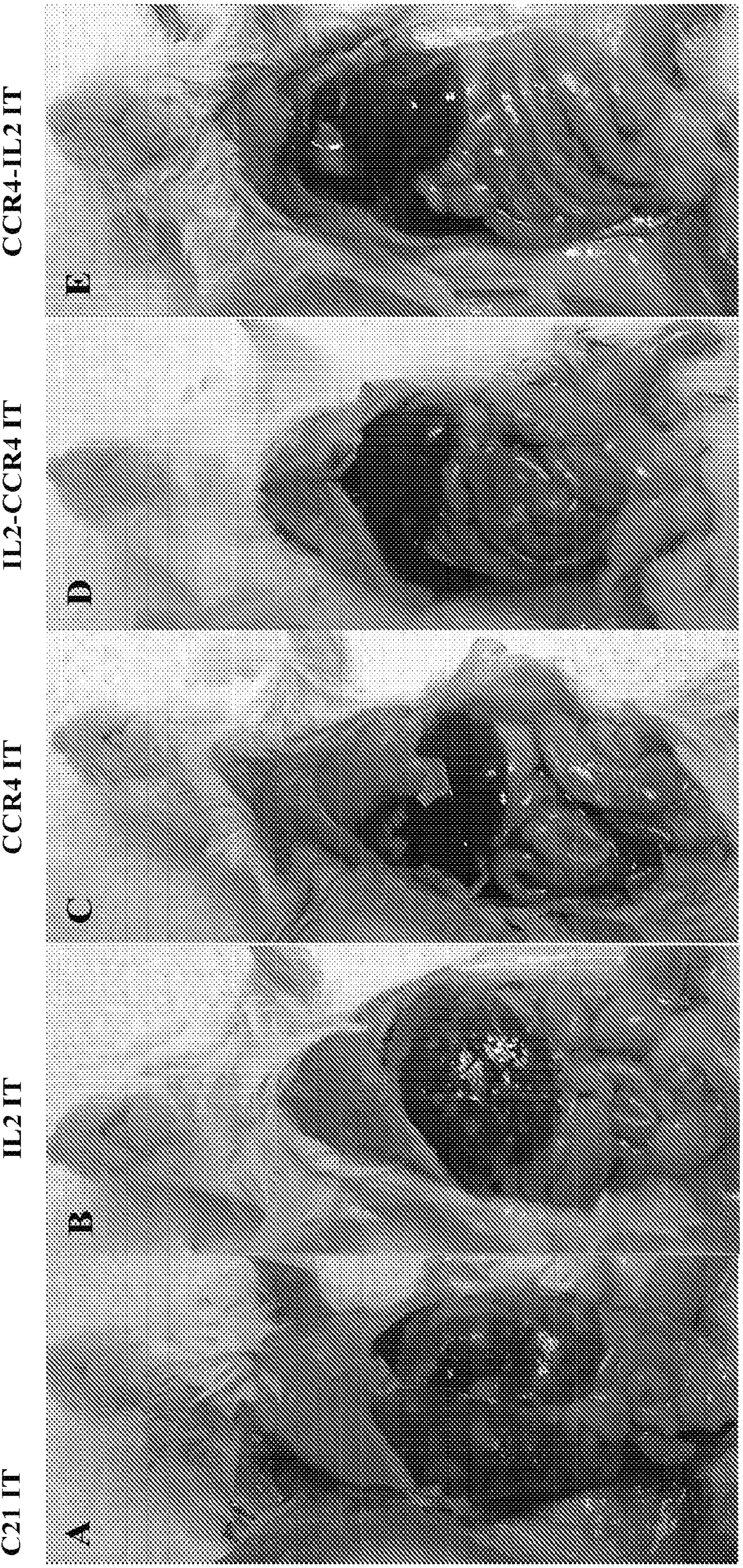
FIG. 8 is a liver necropsy examination of the representative tumor-bearing mice at day 21 from A) C21 immunotoxin group; B) IL2 fusion toxin alone group; C) CCR4 immunotoxin alone group; D) IL2-CCR4 bispecific immunotoxin group; E) CCR4-IL2 bispecific immunotoxin group.
Figure 9:
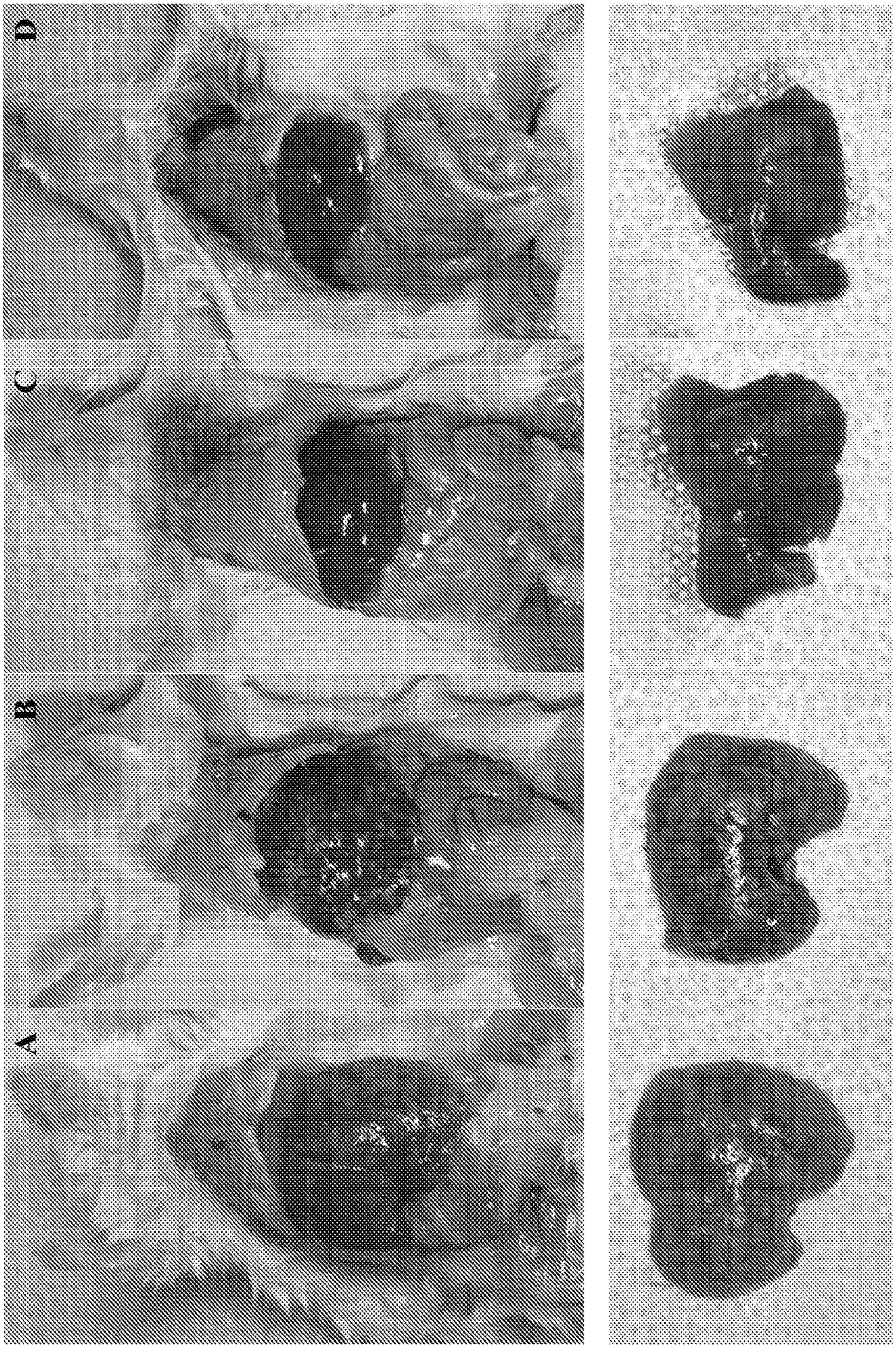
FIG. 9 is a liver necropsy examination (repetition) of the representative tumor-bearing mice at day 21 from A) C21 immunotoxin group; B) IL2 fusion toxin alone group; C) CCR4 immunotoxin alone group; D) CCR4-IL2 bispecific immunotoxin group.
Figure 10:
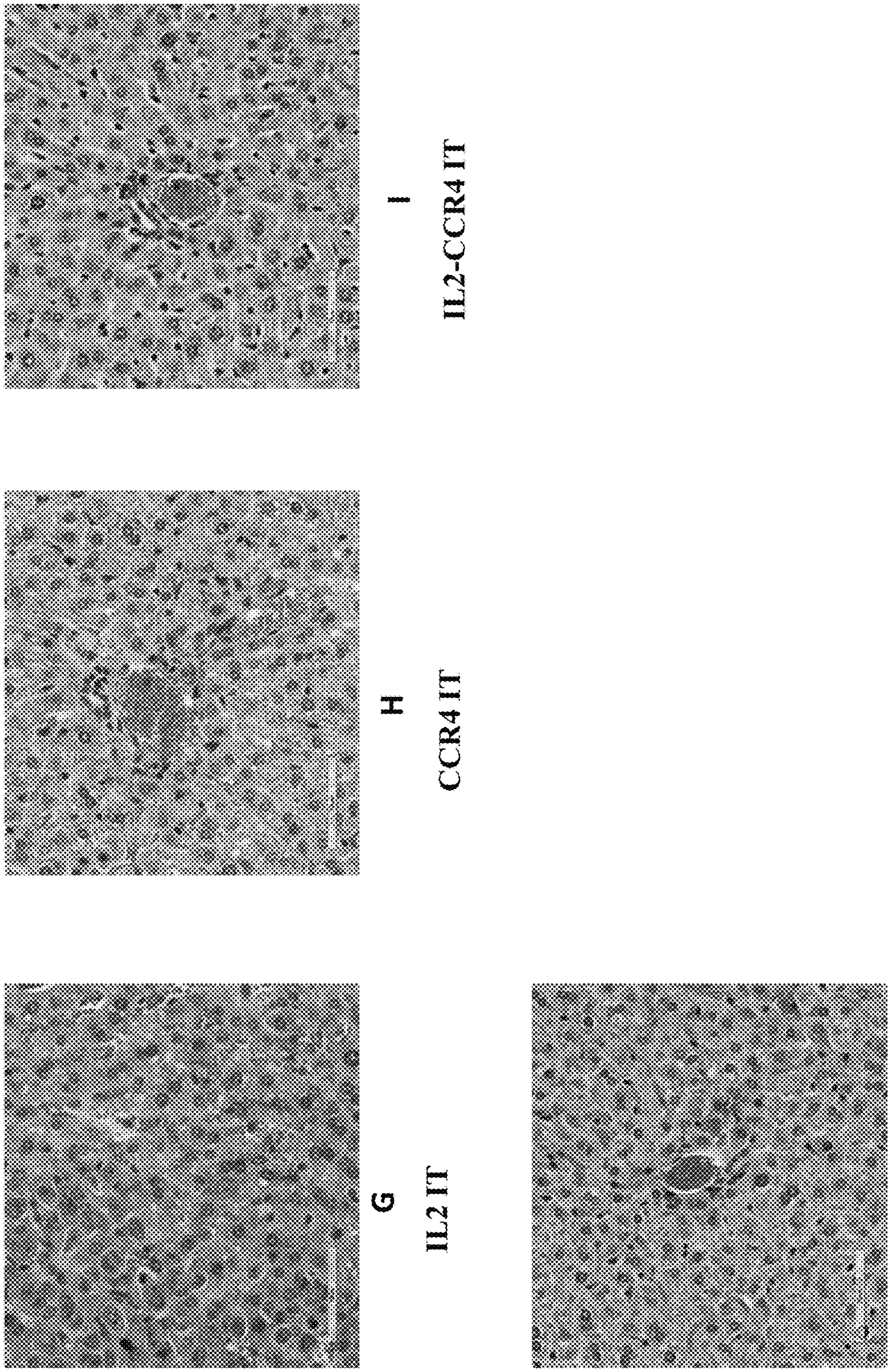
FIG. 10 is a pathology analysis: A) and F) Liver from a mouse injected with both Hut102/6TG tumor cells and C21 immunotoxin (negative control) shows extensive tumor infiltration with replacement of liver parenchyma by tumor cells. B) and G) Liver from a mouse injected with both Hut102/6TG tumor cells and IL2 fusion toxin shows fewer tumor cell areas in the examined section. C) and H) Liver from a mouse injected with both Hut102/6TG and CCR4 immunotoxin shows only a few sporadic tumor nodules. D-E) and I-J) Liver from a mouse injected with both Hut102/6TG and IL2-CCR4 or CCR4-IL2 bispecific immunotoxin shows normal or near normal hepatic parenchyma in the examined section. Two tumor cell areas were observed in the examined section of IL2-CCR4 immunotoxin treated animal liver (D) and none in CCR4-IL2 immunotoxin treated animal liver (E).

Analysis of In Vivo Efficacy of the IL2 Bispecific Immunotoxins Using $CD25^+CCR4^+$ CTCL Hut102/6TG-Bearing Immunodeficient NSG Mouse Model In vivo efficacy of the IL2-CCR4 or CCR4-IL2 bispecific immunotoxin was assessed using $CD25^+CCR4^+$ CTCL Hut102/6TG-bearing immunodeficient NSG mouse model. The tumor cells were intravenously (IV) injected on day 0. The immunotoxins were intraperitoneal (IP) injected starting on day 4 for 10 consecutive days. As shown in FIG. 7, the bispecific immunotoxins significantly prolonged median survival from 24 days in the C21 immunotoxin control group to 57 and 69 days in the IL2-CCR4 and CCR4-IL2 bispecific immunotoxin groups, respectively. This median survival was significantly longer than the median survival of 33.5 and 40 days for IL2 fusion toxin and CCR4 immunotoxin, respectively (FIG. 7, Table 2 and 3). As shown in FIG. 8 and FIG. 9, gross examination during necropsy on day 21 revealed enlarged livers with extensive CTCL tumor nodules on the liver surface of C21 immunotoxin control animals. The IL2 fusion toxin group had less hepatomegaly with fewer tumor nodules when compared with the C21 immunotoxin control group. The CCR4 immunotoxin group and the two bispecific immunotoxin groups demonstrated normal liver size with few sporadic tumor nodules (FIG. 8 and FIG. 9). Histological evaluation of the liver was performed at day 21 for five representative tumor-bearing NSG mice. For the C21 immunotoxin group, hematoxylin and eosin staining revealed replacement of liver parenchyma with extensive tumor nodules. (FIGS. 10A and 10F). In the IL-2 fusion toxin group, fewer tumor cell areas were seen in the examined section of the liver compared to that of the C21 immunotoxin group (FIGS. 10B and 10G). This pathology analysis confirms that the IL2 fusion toxin has efficacy in depletion of human $CD25^+CCR4^+$ tumor cells. Pathology of the CCR4 immunotoxin alone group showed sporadic tumor cell areas (FIGS. 10C and 10H), demonstrating that CCR4 immunotoxin treatment is more effective against the tumor cells than IL2 fusion toxin treatment. In the IL2-CCR4 immunotoxin group (FIGS. 10D and 10I, two tumor cell areas were identified in the examined section of the liver (see FIG. 10D). In the CCR4-IL2 immunotoxin group (FIGS. 10E and 10J), no tumor cell areas were identified in the examined section of the liver (see FIG. 10E), demonstrating that both the IL2-CCR4 and CCR4-IL2 bispecific immunotoxin more effectively depleted the human $CD25^+CCR4^+$ tumor cells than IL2 fusion toxin or CCR4 immunotoxin. Taken together, these in vivo efficacy data consistently demonstrated that CCR4 immunotoxin is more effective than IL2 fusion toxin and that the bispecific immunotoxin showed more efficacy and greater tumor response in vivo than either monospecific CCR4 immunotoxin or IL2 fusion toxin alone.

As shown in FIG. 7, Table 2 and 3, CCR4-IL2 bispecific immunotoxin prolonged the tumor-bearing animal survival significantly longer than IL2-CCR4 bispecific immunotoxin (median survival days of 69 vs 57). The only difference between these two bispecific immunotoxins is the order of IL2 and anti-human CCR4 scFv in the C-terminus of DT390 (either IL2-CCR4 or CCR4-IL2) (see FIG. 1). Histologic analysis demonstrated that two tumor cell areas (FIG. 10D) were identified in the examined section of IL2-CCR4 bispecific immunotoxin treated animal liver. In contrast, no tumor cell area (FIG. 10E) was identified in the examined section of the CCR4-IL2 bispecific immunotoxin treated animal liver. This histology data may explain why CCR4-IL2 immunotoxin lead to longer animal survival than IL2-CCR4 immunotoxin (FIG. 7).

We claim:

1. A bispecific immunotoxin comprising:

a first part comprising a toxin;

a second part comprising a human interleukin (IL-2); and a third part comprising an anti-human CC chemokine Receptor 4 (CCR4) antibody including amino acid sequences SEO ID NOs: 9 and 11, or fragments thereof, the second part being linked to the third part.

2. The bispecific immunotoxin of claim 1, wherein the toxin is diphtheria toxin or a variant thereof.

3. The bispecific immunotoxin of claim 2, wherein the second part is linked to the third part by a linker.

4. The bispecific immunotoxin of claim 3, wherein the first part is linked to the second part.

5. The bispecific immunotoxin of claim 4, wherein the first part is linked to the second part by a linker.

6. The bispecific immunotoxin of claim 5 comprising amino acids 1-791 of SEQ ID NO:4.

7. The bispecific immunotoxin of claim 3, wherein the first part is linked to the third part.

8. The bispecific immunotoxin of claim 7, wherein the first part is linked to the third part by a linker.

9. The bispecific immunotoxin of claim 8 comprising amino acids 1-791 of SEQ ID NO:2.

10. A pharmaceutical composition comprising the bispecific immunotoxin of claim 1, and a physiologically acceptable carrier.

11. A nucleic acid encoding the bispecific immunotoxin of claim 1.

12. The nucleic acid of claim 11, wherein the nucleic acid is a codon-optimized nucleic acid molecule optimized for expression in a methylotropic yeast.

13. A vector comprising the nucleic acid molecule of claim 12.

14. A host cell expressing the nucleic acid molecule of claim 12.

15. The host cell of claim 14, wherein the host cell is a methylotropic yeast.

16. A method of producing a IL2-CCR4 bispecific immunotoxin, the method comprising:

expressing a codon-optimized nucleic acid molecule encoding the bispecific immunotoxin of claim 1 in a methylotropic yeast; and purifying the IL2-CCR4 bispecific immunotoxin, thereby producing the IL2-CCR4 bispecific immunotoxin.

17. A method of treating a subject who has a cancer, the method comprising administering to the subject a therapeutically effective amount of the bispecific immunotoxin of claim 1, wherein the cancer is CD25+ or COR4+, and the treating increases the resistance of the subject to further development an existing cancer, eliminates or at least control the existing cancer, and/or reduces the severity of the existing cancer.

18. The method of claim 17, further comprising administering an immunotherapy to the subject.

19. The method of claim 17, wherein the cancer is selected from a group of CCR4+ and/or CD25+ tumors.

20. A method of depleting CD25-expressing regulatory T cells in a subject, the method comprising administering to the subject an effective amount of the bispecific immunotoxin of claim 1.

* * * * *

SEQUENCE LISTING

<160> NUMBER OF SEQ ID NOS: 20

<210> SEQ ID NO 1
<211> LENGTH: 2391
<212> TYPE: DNA
<213> ORGANISM: Artificial Sequence
<220> FEATURE:
<223> OTHER INFORMATION: CCR4-IL2 bispecific immunotoxin DNA sequence

<400> SEQUENCE: 1
gctggtgctg acgacgtcgt cgactcctcc aagtccttcg tcatggagaa cttcgcttcc 60
taccacggga ccaagccagg ttacgtcgac tccatccaga agggtatcca gaagccaaag 120
tccggcaccc aaggtaacta cgacgacgac tggaaggggt tctactccac cgacaacaag 180
tacgacgctg cgggatactc tgtagataat gaaaacccgc tctctggaaa agctggaggc 240
gtggtcaagg tcacctaccc aggtctgact aaggtcttgg ctttgaaggt cgacaacgct 300
gagaccatca agaaggagtt gggtttgtcc ttgactgagc cattgatgga gcaagtcggt 360
accgaagagt tcatcaagag attcggtgac ggtgcttcca gagtcgtctt gtccttgcca 420
ttcgctgagg gttcttctag cgttgaatat attaataact gggaacaggc taaggctttg 480
tctgttgaat tggagattaa cttcgaaacc agaggtaaga gaggtcaaga tgcgatgtat 540
gagtatatgg ctcaagcctg tgctggtaac agagtcagac gttctgttgg ttcctctttg 600
tcctgtatca acctagactg ggacgtcatc agagacaaga ctaagaccaa gatcgagtct 660
ttgaaagagc atggcccaat caagaacaag atgtccgaat cccccgctaa gaccgtctcc 720
gaggaaaagg ccaagcaata cctagaagag ttccaccaaa ccgccttgga gcatcctgaa 780
ttgtcagaac ttaaaaccgt tactgggacc aatcctgtat tcgctggggc taactatgcg 840
gcgtgggcag taaacgttgc gcaagttatc gatagcgaaa cagctgataa tttggaaaag 900
acaactgctg ctctttcgat acttcctggt atcggtagcg taatgggcat tgcagacggt 960
gccgttcacc acaatacaga agagatagtg gcacaatcca tcgctttgtc ctctttgatg 1020
gttgctcaag ctatcccatt ggtcggtgag ttggttgaca tcggtttcgc tgcctacaac 1080
ttcgtcgagt ccatcatcaa cttgttccaa gtcgtccaca actcctacaa ccgtccggct 1140
tactccccag gtcacaagac ccaaccattc ttgccatggg gtggtggtgg ttctgacatt 1200
gagttgactc aatctccatc ttccttggct gtttctgctg gtgagaaggt tactatgtct 1260
tgtaagtctt cccaatctat tttgtactct tccaaccaaa agaactactt ggcttggtac 1320
caacaaaagc caggtcaatc tccaaagttg ttgatttact gggcttctac tagagagtct 1380
ggtgttccag acagattcac tggttctggt tctggtactg acttcacttt gactatttct 1440
tccgttcaag ctgaggactt ggctgtttac tactgtcacc aatacttgtc ttcctacact 1500
ttcggtggtg gtactaagtt ggagattaag ggtggtggtg gttctggtgg tggtggatct 1560
ggtggtggtg gttctcaagt tcaattgcaa caatctggtc cagagttggt tagaccaggt 1620
gcttctgtta gaatttcttg taaggcttct ggttacactt tcgcttctta ctacattcaa 1680
tggatgaagc aaagaccagg tcaaggtttg gagtggattg gttggattaa cccaggtaac 1740
gttaacacta agtacaacga gaagttcaag ggtaaggcta ctttgactgc tgacaagtct 1800
tccactaccg cttacatgca attgtcttcc ttgacttctg aggactctgc tgtttacttc 1860
tgtgctagat ccacttacta cagaccattg gactactggg gtcaaggtac taccgttact 1920
gtttcttccg gtggtggtgg ttctggtggt ggtggatccg gtggtggtgg ttctgctcca 1980
acttcttctt ctactaagaa gactcaattg caattggagc acttgttgtt ggacttgcaa 2040
atgattttga acggtattaa caactacaag aacccaaagt tgactagaat gttgactttc 2100
aagttctaca tgccaaagaa ggctactgag ttgaagcact tgcaatgttt ggaggaggaa 2160
ttgaagccat tggaggaagt tttgaacttg gctcaatcta agaacttcca cttgagacca 2220
agagacttga tttctaacat taacgttatt gttttggagt tgaagggttc tgagactact 2280
ttcatgtgtg agtacgctga cgagactgct actattgttg agttcttgaa cagatggatt 2340
actttctgtc aatctattat ctctactttg actcaccacc accaccacca c 2391

<210> SEQ ID NO 2
<211> LENGTH: 797
<212> TYPE: PRT
<213> ORGANISM: Artificial Sequence
<220> FEATURE:
<223> OTHER INFORMATION: CCR4-IL2 bispecific immunotoxin amino acid sequence

<400> SEQUENCE: 2

Ala Gly Ala Asp Asp Val Val Asp Ser Ser Lys Ser Phe Val Met Glu
1 5 10 15

Asn Phe Ala Ser Tyr His Gly Thr Lys Pro Gly Tyr Val Asp Ser Ile
20 25 30

Gln Lys Gly Ile Gln Lys Pro Lys Ser Gly Thr Gln Gly Asn Tyr Asp
35 40 45

Asp Asp Trp Lys Gly Phe Tyr Ser Thr Asp Asn Lys Tyr Asp Ala Ala
50 55 60

Gly Tyr Ser Val Asp Asn Glu Asn Pro Leu Ser Gly Lys Ala Gly Gly
65 70 75 80

Val Val Lys Val Thr Tyr Pro Gly Leu Thr Lys Val Leu Ala Leu Lys
85 90 95

Val Asp Asn Ala Glu Thr Ile Lys Lys Glu Leu Gly Leu Ser Leu Thr
100 105 110

Glu Pro Leu Met Glu Gln Val Gly Thr Glu Glu Phe Ile Lys Arg Phe
115 120 125

Gly Asp Gly Ala Ser Arg Val Val Leu Ser Leu Pro Phe Ala Glu Gly
130 135 140

Ser Ser Ser Val Glu Tyr Ile Asn Asn Trp Glu Gln Ala Lys Ala Leu
145 150 155 160

Ser Val Glu Leu Glu Ile Asn Phe Glu Thr Arg Gly Lys Arg Gly Gln
165 170 175

Asp Ala Met Tyr Glu Tyr Met Ala Gln Ala Cys Ala Gly Asn Arg Val
180 185 190

Arg Arg Ser Val Gly Ser Ser Leu Ser Cys Ile Asn Leu Asp Trp Asp
195 200 205

Val Ile Arg Asp Lys Thr Lys Thr Lys Ile Glu Ser Leu Lys Glu His
210 215 220

Gly Pro Ile Lys Asn Lys Met Ser Glu Ser Pro Ala Lys Thr Val Ser

-continued

```
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Leu Pro Trp Gly Gly Gly Gly Ser Asp Ile
385                 390                 395                 400

Glu Leu Thr Gln Ser Pro Ser Ser Leu Ala Val Ser Ala Gly Glu Lys
                405                 410                 415

Val Thr Met Ser Cys Lys Ser Ser Gln Ser Ile Leu Tyr Ser Ser Asn
            420                 425                 430

Gln Lys Asn Tyr Leu Ala Trp Tyr Gln Gln Lys Pro Gly Gln Ser Pro
        435                 440                 445

Lys Leu Leu Ile Tyr Trp Ala Ser Thr Arg Glu Ser Gly Val Pro Asp
    450                 455                 460

Arg Phe Thr Gly Ser Gly Ser Gly Thr Asp Phe Thr Leu Thr Ile Ser
465                 470                 475                 480

Ser Val Gln Ala Glu Asp Leu Ala Val Tyr Tyr Cys His Gln Tyr Leu
                485                 490                 495

Ser Ser Tyr Thr Phe Gly Gly Gly Thr Lys Leu Glu Ile Lys Gly Gly
            500                 505                 510

Gly Gly Ser Gly Gly Gly Gly Ser Gly Gly Gly Gly Ser Gln Val Gln
        515                 520                 525

Leu Gln Gln Ser Gly Pro Glu Leu Val Arg Pro Gly Ala Ser Val Arg
    530                 535                 540

Ile Ser Cys Lys Ala Ser Gly Tyr Thr Phe Ala Ser Tyr Tyr Ile Gln
545                 550                 555                 560

Trp Met Lys Gln Arg Pro Gly Gln Gly Leu Glu Trp Ile Gly Trp Ile
                565                 570                 575

Asn Pro Gly Asn Val Asn Thr Lys Tyr Asn Glu Lys Phe Lys Gly Lys
            580                 585                 590

Ala Thr Leu Thr Ala Asp Lys Ser Ser Thr Thr Ala Tyr Met Gln Leu
        595                 600                 605

Ser Ser Leu Thr Ser Glu Asp Ser Ala Val Tyr Phe Cys Ala Arg Ser
    610                 615                 620

Thr Tyr Tyr Arg Pro Leu Asp Tyr Trp Gly Gln Gly Thr Thr Val Thr
625                 630                 635                 640

Val Ser Ser Gly Gly Gly Gly Ser Gly Gly Gly Gly Ser Gly Gly Gly
                645                 650                 655
```

```
Gly Ser Ala Pro Thr Ser Ser Ser Thr Lys Lys Thr Gln Leu Gln Leu
            660                 665                 670

Glu His Leu Leu Leu Asp Leu Gln Met Ile Leu Asn Gly Ile Asn Asn
        675                 680                 685

Tyr Lys Asn Pro Lys Leu Thr Arg Met Leu Thr Phe Lys Phe Tyr Met
    690                 695                 700

Pro Lys Lys Ala Thr Glu Leu Lys His Leu Gln Cys Leu Glu Glu Glu
705                 710                 715                 720

Leu Lys Pro Leu Glu Glu Val Leu Asn Leu Ala Gln Ser Lys Asn Phe
                725                 730                 735

His Leu Arg Pro Arg Asp Leu Ile Ser Asn Ile Asn Val Ile Val Leu
            740                 745                 750

Glu Leu Lys Gly Ser Glu Thr Thr Phe Met Cys Glu Tyr Ala Asp Glu
        755                 760                 765

Thr Ala Thr Ile Val Glu Phe Leu Asn Arg Trp Ile Thr Phe Cys Gln
    770                 775                 780

Ser Ile Ile Ser Thr Leu Thr His His His His His His
785                 790                 795


<210> SEQ ID NO 3
<211> LENGTH: 2391
<212> TYPE: DNA
<213> ORGANISM: Artificial Sequence
<220> FEATURE:
<223> OTHER INFORMATION: IL2-CCR4 bispecific immunotoxin DNA sequence

<400> SEQUENCE: 3

gctggtgctg acgacgtcgt cgactcctcc aagtccttcg tcatggagaa cttcgcttcc     60

taccacggga ccaagccagg ttacgtcgac tccatccaga agggtatcca gaagccaaag    120

tccggcaccc aaggtaacta cgacgacgac tggaaggggt tctactccac cgacaacaag    180

tacgacgctg cgggatactc tgtagataat gaaaacccgc tctctggaaa agctggaggc    240

gtggtcaagg tcacctaccc aggtctgact aaggtcttgg ctttgaaggt cgacaacgct    300

gagaccatca agaaggagtt gggtttgtcc ttgactgagc cattgatgga gcaagtcggt    360

accgaagagt tcatcaagag attcggtgac ggtgcttcca gagtcgtctt gtccttgcca    420

ttcgctgagg gttcttctag cgttgaatat attaataact gggaacaggc taaggctttg    480

tctgttgaat tggagattaa cttcgaaacc agaggtaaga gaggtcaaga tgcgatgtat    540

gagtatatgg ctcaagcctg tgctggtaac agagtcagac gttctgttgg ttcctctttg    600

tcctgtatca acctagactg ggacgtcatc agagacaaga ctaagaccaa gatcgagtct    660

ttgaaagagc atggcccaat caagaacaag atgtccgaat cccccgctaa gaccgtctcc    720

gaggaaaagg ccaagcaata cctagaagag ttccaccaaa ccgccttgga gcatcctgaa    780

ttgtcagaac ttaaaaccgt tactgggacc aatcctgtat tcgctggggc taactatgcg    840

gcgtgggcag taaacgttgc gcaagttatc gatagcgaaa cagctgataa tttggaaaag    900

acaactgctg ctctttcgat acttcctggt atcggtagcg taatgggcat tgcagacggt    960

gccgttcacc acaatacaga agagatagtg gcacaatcca tcgctttgtc ctctttgatg   1020

gttgctcaag ctatcccatt ggtcggtgag ttggttgaca tcggtttcgc tgcctacaac   1080

ttcgtcgagt ccatcatcaa cttgttccaa gtcgtccaca actcctacaa ccgtccggct   1140

tactccccag gtcacaagac ccaaccattc ttgccatggg gtggtggtgg ttctgctcca   1200

acttcttctt ctactaagaa gactcaattg caattggagc acttgttgtt ggacttgcaa   1260
```

```
atgattttga acggtattaa caactacaag aacccaaagt tgactagaat gttgactttc   1320

aagttctaca tgccaaagaa ggctactgag ttgaagcact tgcaatgttt ggaggaggaa   1380

ttgaagccat tggaggaagt tttgaacttg gctcaatcta agaacttcca cttgagacca   1440

agagacttga tttctaacat taacgttatt gttttggagt tgaagggttc tgagactact   1500

ttcatgtgtg agtacgctga cgagactgct actattgttg agttcttgaa cagatggatt   1560

actttctgtc aatctattat ctctactttg actggtggtg gtggttctgg tggtggtgga   1620

tccggtggtg gtggttctga cattgagttg actcaatctc catcttcctt ggctgtttct   1680

gctggtgaga aggttactat gtcttgtaag tcttcccaat ctattttgta ctcttccaac   1740

caaaagaact acttggcttg gtaccaacaa aagccaggtc aatctccaaa gttgttgatt   1800

tactgggctt ctactagaga gtctggtgtt ccagacagat tcactggttc tggttctggt   1860

actgacttca ctttgactat ttcttccgtt caagctgagg acttggctgt ttactactgt   1920

caccaatact tgtcttccta cactttcggt ggtggtacta agttggagat taagggtggt   1980

ggtggttctg gtggtggtgg atctggtggt ggtggttctc aagttcaatt gcaacaatct   2040

ggtccagagt tggttagacc aggtgcttct gttagaattt cttgtaaggc ttctggttac   2100

actttcgctt cttactacat tcaatggatg aagcaaagac caggtcaagg tttggagtgg   2160

attggttgga ttaacccagg taacgttaac actaagtaca acgagaagtt caagggtaag   2220

gctactttga ctgctgacaa gtcttccact accgcttaca tgcaattgtc ttccttgact   2280

tctgaggact ctgctgttta cttctgtgct agatccactt actacagacc attggactac   2340

tggggtcaag gtactaccgt tactgtttct tcccaccacc accaccacca c             2391
```

```
<210> SEQ ID NO 4
<211> LENGTH: 797
<212> TYPE: PRT
<213> ORGANISM: Artificial Sequence
<220> FEATURE:
<223> OTHER INFORMATION: IL2-CCR4 bispecific immunotoxin amino acid
      sequence

<400> SEQUENCE: 4

Ala Gly Ala Asp Asp Val Val Asp Ser Ser Lys Ser Phe Val Met Glu
1               5                   10                  15

Asn Phe Ala Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160
```

-continued

```
Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Leu Pro Trp Gly Gly Gly Gly Ser Ala Pro
385                 390                 395                 400

Thr Ser Ser Ser Thr Lys Lys Thr Gln Leu Gln Leu Glu His Leu Leu
                405                 410                 415

Leu Asp Leu Gln Met Ile Leu Asn Gly Ile Asn Asn Tyr Lys Asn Pro
            420                 425                 430

Lys Leu Thr Arg Met Leu Thr Phe Lys Phe Tyr Met Pro Lys Lys Ala
        435                 440                 445

Thr Glu Leu Lys His Leu Gln Cys Leu Glu Glu Glu Leu Lys Pro Leu
    450                 455                 460

Glu Glu Val Leu Asn Leu Ala Gln Ser Lys Asn Phe His Leu Arg Pro
465                 470                 475                 480

Arg Asp Leu Ile Ser Asn Ile Asn Val Ile Val Leu Glu Leu Lys Gly
                485                 490                 495

Ser Glu Thr Thr Phe Met Cys Glu Tyr Ala Asp Glu Thr Ala Thr Ile
            500                 505                 510

Val Glu Phe Leu Asn Arg Trp Ile Thr Phe Cys Gln Ser Ile Ile Ser
        515                 520                 525

Thr Leu Thr Gly Gly Gly Gly Ser Gly Gly Gly Gly Ser Gly Gly Gly
    530                 535                 540

Gly Ser Asp Ile Glu Leu Thr Gln Ser Pro Ser Ser Leu Ala Val Ser
545                 550                 555                 560

Ala Gly Glu Lys Val Thr Met Ser Cys Lys Ser Ser Gln Ser Ile Leu
                565                 570                 575
```

-continued

```
Tyr Ser Ser Asn Gln Lys Asn Tyr Leu Ala Trp Tyr Gln Gln Lys Pro
            580                 585                 590

Gly Gln Ser Pro Lys Leu Leu Ile Tyr Trp Ala Ser Thr Arg Glu Ser
        595                 600                 605

Gly Val Pro Asp Arg Phe Thr Gly Ser Gly Ser Gly Thr Asp Phe Thr
    610                 615                 620

Leu Thr Ile Ser Ser Val Gln Ala Glu Asp Leu Ala Val Tyr Tyr Cys
625                 630                 635                 640

His Gln Tyr Leu Ser Ser Tyr Thr Phe Gly Gly Gly Thr Lys Leu Glu
                645                 650                 655

Ile Lys Gly Gly Gly Gly Ser Gly Gly Gly Gly Ser Gly Gly Gly Gly
            660                 665                 670

Ser Gln Val Gln Leu Gln Gln Ser Gly Pro Glu Leu Val Arg Pro Gly
        675                 680                 685

Ala Ser Val Arg Ile Ser Cys Lys Ala Ser Gly Tyr Thr Phe Ala Ser
    690                 695                 700

Tyr Tyr Ile Gln Trp Met Lys Gln Arg Pro Gly Gln Gly Leu Glu Trp
705                 710                 715                 720

Ile Gly Trp Ile Asn Pro Gly Asn Val Asn Thr Lys Tyr Asn Glu Lys
                725                 730                 735

Phe Lys Gly Lys Ala Thr Leu Thr Ala Asp Lys Ser Ser Thr Thr Ala
            740                 745                 750

Tyr Met Gln Leu Ser Ser Leu Thr Ser Glu Asp Ser Ala Val Tyr Phe
        755                 760                 765

Cys Ala Arg Ser Thr Tyr Tyr Arg Pro Leu Asp Tyr Trp Gly Gln Gly
    770                 775                 780

Thr Thr Val Thr Val Ser Ser His His His His His His
785                 790                 795


<210> SEQ ID NO 5
<211> LENGTH: 230
<212> TYPE: PRT
<213> ORGANISM: Artificial Sequence
<220> FEATURE:
<223> OTHER INFORMATION: Rearranged mouse variable heavy (VH) and
      variable light (VL) K domains of mAb1567

<400> SEQUENCE: 5

Gln Val Gln Leu Gln Gln Ser Gly Pro Glu Leu Val Arg Pro Gly Ala
1               5                   10                  15

Ser Val Arg Ile Ser Cys Lys Ala Ser Gly Tyr Thr Phe Ala Ser Tyr
            20                  25                  30

Tyr Ile Gln Trp Met Lys Gln Arg Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Ser Thr Tyr Tyr Arg Pro Leu Asp Tyr Trp Gly Gln Gly Thr
            100                 105                 110

Thr Val Thr Val Ser Ser Asp Ile Glu Leu Thr Gln Ser Pro Ser Ser
        115                 120                 125

Leu Ala Val Ser Ala Gly Glu Lys Val Thr Met Ser Cys Lys Ser Ser
    130                 135                 140
```

-continued

```
Gln Ser Ile Leu Tyr Ser Ser Asn Gln Lys Asn Tyr Leu Ala Trp Tyr
145                 150                 155                 160

Gln Gln Lys Pro Gly Gln Ser Pro Lys Leu Leu Ile Tyr Trp Ala Ser
                165                 170                 175

Thr Arg Glu Ser Gly Val Pro Asp Arg Phe Thr Gly Ser Gly Ser Gly
            180                 185                 190

Thr Asp Phe Thr Leu Thr Ile Ser Ser Val Gln Ala Glu Asp Leu Ala
        195                 200                 205

Val Tyr Tyr Cys His Gln Tyr Leu Ser Ser Tyr Thr Phe Gly Gly Gly
    210                 215                 220

Thr Lys Leu Glu Ile Lys
225                 230


<210> SEQ ID NO 6
<211> LENGTH: 230
<212> TYPE: PRT
<213> ORGANISM: Artificial Sequence
<220> FEATURE:
<223> OTHER INFORMATION: Humanized variable heavy (VH) and variable
      light (VK) K domains of mAb1567

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
            20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
            100                 105                 110

Leu Val Thr Val Ser Ser Asp Ile Val Met Thr Gln Ser Pro Asp Ser
        115                 120                 125

Leu Ala Val Ser Leu Gly Glu Arg Ala Thr Ile Asn Cys Lys Ser Ser
    130                 135                 140

Gln Ser Ile Leu Tyr Ser Ser Asn Gln Lys Asn Tyr Leu Ala Trp Tyr
145                 150                 155                 160

Gln Gln Lys Pro Gly Gln Ser Pro Lys Leu Leu Ile Tyr Trp Ala Ser
                165                 170                 175

Thr Arg Glu Ser Gly Val Pro Asp Arg Phe Ser Gly Ser Gly Ser Gly
            180                 185                 190

Thr Asp Phe Thr Leu Thr Ile Ser Ser Leu Gln Ala Glu Asp Val Ala
        195                 200                 205

Val Tyr Tyr Cys His Gln Tyr Leu Ser Ser Tyr Thr Phe Gly Gln Gly
    210                 215                 220

Thr Lys Leu Glu Ile Lys
225                 230


<210> SEQ ID NO 7
<211> LENGTH: 1179
<212> TYPE: DNA
```

<213> ORGANISM: Artificial Sequence
<220> FEATURE:
<223> OTHER INFORMATION: DT 390 DNA sequence

<400> SEQUENCE: 7
gctggtgctg acgacgtcgt cgactcctcc aagtccttcg tcatggagaa cttcgcttcc 60
taccacggga ccaagccagg ttacgtcgac tccatccaga agggtatcca gaagccaaag 120
tccggcaccc aaggtaacta cgacgacgac tggaaggggt tctactccac cgacaacaag 180
tacgacgctg cgggatactc tgtagataat gaaaacccgc tctctggaaa agctggaggc 240
gtggtcaagg tcacctaccc aggtctgact aaggtcttgg ctttgaaggt cgacaacgct 300
gagaccatca agaaggagtt gggtttgtcc ttgactgagc cattgatgga gcaagtcggt 360
accgaagagt tcatcaagag attcggtgac ggtgcttcca gagtcgtctt gtccttgcca 420
ttcgctgagg gttcttctag cgttgaatat attaataact gggaacaggc taaggctttg 480
tctgttgaat tggagattaa cttcgaaacc agaggtaaga gaggtcaaga tgcgatgtat 540
gagtatatgg ctcaagcctg tgctggtaac agagtcagac gttctgttgg ttcctctttg 600
tcctgtatca acctagactg ggacgtcatc agagacaaga ctaagaccaa gatcgagtct 660
ttgaaagagc atggcccaat caagaacaag atgtccgaat cccccgctaa gaccgtctcc 720
gaggaaaagg ccaagcaata cctagaagag ttccaccaaa ccgccttgga gcatcctgaa 780
ttgtcagaac ttaaaaccgt tactgggacc aatcctgtat tcgctggggc taactatgcg 840
gcgtgggcag taaacgttgc gcaagttatc gatagcgaaa cagctgataa tttggaaaag 900
acaactgctg ctctttcgat acttcctggt atcggtagcg taatgggcat tgcagacggt 960
gccgttcacc acaatacaga agagatagtg gcacaatcca tcgctttgtc ctctttgatg 1020
gttgctcaag ctatcccatt ggtcggtgag ttggttgaca tcggtttcgc tgcctacaac 1080
ttcgtcgagt ccatcatcaa cttgttccaa gtcgtccaca actcctacaa ccgtccggct 1140
tactccccag gtcacaagac ccaaccattc ttgccatgg 1179

<210> SEQ ID NO 8
<211> LENGTH: 15
<212> TYPE: DNA
<213> ORGANISM: Artificial Sequence
<220> FEATURE:
<223> OTHER INFORMATION: Linker sequence

<400> SEQUENCE: 8
ggtggtggtg gttct 15

<210> SEQ ID NO 9
<211> LENGTH: 336
<212> TYPE: DNA
<213> ORGANISM: Artificial Sequence
<220> FEATURE:
<223> OTHER INFORMATION: anti-human CCR4 scFv VL

<400> SEQUENCE: 9
gacattgagt tgactcaatc tccatcttcc ttggctgttt ctgctggtga gaaggttact 60
atgtcttgta agtcttccca atctattttg tactcttcca accaaaagaa ctacttggct 120
tggtaccaac aaaagccagg tcaatctcca aagttgttga tttactgggc ttctactaga 180
gagtctggtg ttccagacag attcactggt tctggttctg gtactgactt cactttgact 240
atttcttccg ttcaagctga ggacttggct gtttactact gtcaccaata cttgtcttcc 300
tacactttcg gtggtggtac taagttggag attaag 336

<210> SEQ ID NO 10
<211> LENGTH: 45
<212> TYPE: DNA
<213> ORGANISM: Artificial Sequence
<220> FEATURE:
<223> OTHER INFORMATION: linker sequence

<400> SEQUENCE: 10
ggtggtggtg gttctggtgg tggtggatct ggtggtggtg gttct 45

<210> SEQ ID NO 11
<211> LENGTH: 354
<212> TYPE: DNA
<213> ORGANISM: Artificial Sequence
<220> FEATURE:
<223> OTHER INFORMATION: anti-human CCR4 scFv VH

<400> SEQUENCE: 11
caagttcaat tgcaacaatc tggtccagag ttggttagac caggtgcttc tgttagaatt 60
tcttgtaagg cttctggtta cactttcgct tcttactaca ttcaatggat gaagcaaaga 120
ccaggtcaag gtttggagtg gattggttgg attaacccag gtaacgttaa cactaagtac 180
aacgagaagt tcaagggtaa ggctactttg actgctgaca agtcttccac taccgcttac 240
atgcaattgt cttccttgac ttctgaggac tctgctgttt acttctgtgc tagatccact 300
tactacagac cattggacta ctggggtcaa ggtactaccg ttactgtttc ttcc 354

<210> SEQ ID NO 12
<211> LENGTH: 45
<212> TYPE: DNA
<213> ORGANISM: Artificial Sequence
<220> FEATURE:
<223> OTHER INFORMATION: linker sequence

<400> SEQUENCE: 12
ggtggtggtg gttctggtgg tggtggatcc ggtggtggtg gttct 45

<210> SEQ ID NO 13
<211> LENGTH: 417
<212> TYPE: DNA
<213> ORGANISM: Homo sapiens

<400> SEQUENCE: 13
gctccaactt cttcttctac taagaagact caattgcaat tggagcactt gttgttggac 60
ttgcaaatga ttttgaacgg tattaacaac tacaagaacc caaagttgac tagaatgttg 120
actttcaagt tctacatgcc aaagaaggct actgagttga agcacttgca atgtttggag 180
gaggaattga agccattgga ggaagttttg aacttggctc aatctaagaa cttccacttg 240
agaccaagag acttgatttc taacattaac gttattgttt tggagttgaa gggttctgag 300
actactttca tgtgtgagta cgctgacgag actgctacta ttgttgagtt cttgaacaga 360
tggattactt tctgtcaatc tattatctct actttgactc accaccacca ccaccac 417

<210> SEQ ID NO 14
<211> LENGTH: 1179
<212> TYPE: DNA
<213> ORGANISM: Artificial Sequence
<220> FEATURE:
<223> OTHER INFORMATION: DT390

<400> SEQUENCE: 14

-continued

```
gctggtgctg acgacgtcgt cgactcctcc aagtccttcg tcatggagaa cttcgcttcc     60

taccacggga ccaagccagg ttacgtcgac tccatccaga agggtatcca gaagccaaag    120

tccggcaccc aaggtaacta cgacgacgac tggaaggggt tctactccac cgacaacaag    180

tacgacgctg cgggatactc tgtagataat gaaaacccgc tctctggaaa agctggaggc    240

gtggtcaagg tcacctaccc aggtctgact aaggtcttgg ctttgaaggt cgacaacgct    300

gagaccatca agaaggagtt gggtttgtcc ttgactgagc cattgatgga gcaagtcggt    360

accgaagagt tcatcaagag attcggtgac ggtgcttcca gagtcgtctt gtccttgcca    420

ttcgctgagg gttcttctag cgttgaatat attaataact gggaacaggc taaggctttg    480

tctgttgaat tggagattaa cttcgaaacc agaggtaaga gaggtcaaga tgcgatgtat    540

gagtatatgg ctcaagcctg tgctggtaac agagtcagac gttctgttgg ttcctctttg    600

tcctgtatca acctagactg ggacgtcatc agagacaaga ctaagaccaa gatcgagtct    660

ttgaaagagc atggcccaat caagaacaag atgtccgaat cccccgctaa gaccgtctcc    720

gaggaaaagg ccaagcaata cctagaagag ttccaccaaa ccgccttgga gcatcctgaa    780

ttgtcagaac ttaaaaccgt tactgggacc aatcctgtat tcgctggggc taactatgcg    840

gcgtgggcag taaacgttgc gcaagttatc gatagcgaaa cagctgataa tttggaaaag    900

acaactgctg ctctttcgat acttcctggt atcggtagcg taatgggcat tgcagacggt    960

gccgttcacc acaatacaga agagatagtg gcacaatcca tcgctttgtc ctctttgatg   1020

gttgctcaag ctatcccatt ggtcggtgag ttggttgaca tcggtttcgc tgcctacaac   1080

ttcgtcgagt ccatcatcaa cttgttccaa gtcgtccaca actcctacaa ccgtccggct   1140

tactccccag gtcacaagac ccaaccattc ttgccatgg                          1179
```

<210> SEQ ID NO 15
<211> LENGTH: 15
<212> TYPE: DNA
<213> ORGANISM: Artificial Sequence
<220> FEATURE:
<223> OTHER INFORMATION: linker sequence

<400> SEQUENCE: 15

```
ggtggtggtg gttct                                                      15
```

<210> SEQ ID NO 16
<211> LENGTH: 399
<212> TYPE: DNA
<213> ORGANISM: Homo sapiens

<400> SEQUENCE: 16

```
gctccaactt cttcttctac taagaagact caattgcaat tggagcactt gttgttggac     60

ttgcaaatga ttttgaacgg tattaacaac tacaagaacc caaagttgac tagaatgttg    120

actttcaagt tctacatgcc aaagaaggct actgagttga agcacttgca atgtttggag    180

gaggaattga agccattgga ggaagttttg aacttggctc aatctaagaa cttccacttg    240

agaccaagag acttgatttc taacattaac gttattgttt tggagttgaa gggttctgag    300

actactttca tgtgtgagta cgctgacgag actgctacta ttgttgagtt cttgaacaga    360

tggattactt tctgtcaatc tattatctct actttgact                           399
```

<210> SEQ ID NO 17
<211> LENGTH: 45
<212> TYPE: DNA
<213> ORGANISM: Artificial Sequence -continued

```
<220> FEATURE:
<223> OTHER INFORMATION: linker sequence

<400> SEQUENCE: 17

ggtggtggtg gttctggtgg tggtggatcc ggtggtggtg gttct                    45


<210> SEQ ID NO 18
<211> LENGTH: 336
<212> TYPE: DNA
<213> ORGANISM: Artificial Sequence
<220> FEATURE:
<223> OTHER INFORMATION: anti-human CCR4 scFv VL

<400> SEQUENCE: 18

gacattgagt tgactcaatc tccatcttcc ttggctgttt ctgctggtga gaaggttact     60

atgtcttgta agtcttccca atctattttg tactcttcca accaaaagaa ctacttggct    120

tggtaccaac aaaagccagg tcaatctcca aagttgttga tttactgggc ttctactaga    180

gagtctggtg ttccagacag attcactggt tctggttctg gtactgactt cactttgact    240

atttcttccg ttcaagctga ggacttggct gtttactact gtcaccaata cttgtcttcc    300

tacactttcg gtggtggtac taagttggag attaag                              336


<210> SEQ ID NO 19
<211> LENGTH: 45
<212> TYPE: DNA
<213> ORGANISM: Artificial Sequence
<220> FEATURE:
<223> OTHER INFORMATION: linker sequence

<400> SEQUENCE: 19

ggtggtggtg gttctggtgg tggtggatct ggtggtggtg gttct                    45


<210> SEQ ID NO 20
<211> LENGTH: 372
<212> TYPE: DNA
<213> ORGANISM: Artificial Sequence
<220> FEATURE:
<223> OTHER INFORMATION: anti-human CCR4 scFv VH

<400> SEQUENCE: 20

caagttcaat tgcaacaatc tggtccagag ttggttagac caggtgcttc tgttagaatt     60

tcttgtaagg cttctggtta cactttcgct tcttactaca ttcaatggat gaagcaaaga    120

ccaggtcaag gtttggagtg gattggttgg attaacccag gtaacgttaa cactaagtac    180

aacgagaagt tcaagggtaa ggctactttg actgctgaca agtcttccac taccgcttac    240

atgcaattgt cttccttgac ttctgaggac tctgctgttt acttctgtgc tagatccact    300

tactacagac cattggacta ctggggtcaa ggtactaccg ttactgtttc ttcccaccac    360

caccaccacc ac                                                        372
```